United States Patent
Chou et al.

(10) Patent No.: US 12,350,680 B2
(45) Date of Patent: Jul. 8, 2025

(54) ASSAY WITH RAPID TEMPERATURE CHANGE

(71) Applicant: Essenlix Corporation, Monmouth Junction, NJ (US)

(72) Inventors: Stephen Y. Chou, Princeton, NJ (US); Wei Ding, East Windsor, NJ (US); Yufan Zhang, Monmouth Junction, NJ (US); Ji Qi, Hillsborough, NJ (US)

(73) Assignee: Essenlix Corporation, Monmouth Junction, NJ (US)

( * ) Notice: Subject to any disclaimer, the term of this patent is extended or adjusted under 35 U.S.C. 154(b) by 817 days.

(21) Appl. No.: 16/484,998

(22) PCT Filed: Feb. 15, 2018

(86) PCT No.: PCT/US2018/018405
§ 371 (c)(1),
(2) Date: Aug. 9, 2019

(87) PCT Pub. No.: WO2018/152357
PCT Pub. Date: Aug. 23, 2018

(65) Prior Publication Data
US 2020/0078792 A1    Mar. 12, 2020

Related U.S. Application Data

(63) Continuation of application No. PCT/US2018/018108, filed on Feb. 14, 2018, and a
(Continued)

(51) Int. Cl.
*B01L 7/00* (2006.01)
*B01L 3/00* (2006.01)
*C12Q 1/686* (2018.01)

(52) U.S. Cl.
CPC ............... *B01L 7/52* (2013.01); *B01L 3/508* (2013.01); *C12Q 1/686* (2013.01);
(Continued)

(58) Field of Classification Search
CPC ...... B01L 7/52; B01L 3/508; B01L 2200/147; B01L 2300/06; B01L 2300/0627;
(Continued)

(56) References Cited

U.S. PATENT DOCUMENTS 3,368,872 A    2/1968  Natelson
3,447,863 A    6/1969  Patterson
(Continued)

FOREIGN PATENT DOCUMENTS

AU    198813789    9/1988
AU    619459    1/1992
(Continued)

OTHER PUBLICATIONS

Van Vliet, Dillys et al., Prediction of asthma exacerbations in children by innovative exhaled inflammatory markers: Results of a longitudinal study, PLOS One, Mar. 23, 2015, vol. 10. No. 3, e0119434.
(Continued)

*Primary Examiner* — Jill A Warden
*Assistant Examiner* — Jacqueline Brazin

(57) ABSTRACT

The present invention provides devices, systems, and methods for rapid and easy-to-use in sample thermal cycling or temperature changes for the facilitation of reactions such as but not limited to PCR.

90 Claims, 6 Drawing Sheets

Related U.S. Application Data continuation of application No. PCT/US2018/018007, filed on Feb. 13, 2018, and a continuation of application No. PCT/US2018/017712, filed on Feb. 9, 2018, and a continuation of application No. PCT/US2018/017713, filed on Feb. 9, 2018, and a continuation of application No. PCT/US2018/017716, filed on Feb. 9, 2018, and a continuation of application No. PCT/US2018/017489, filed on Feb. 8, 2018, and a continuation of application No. PCT/US2018/017494, filed on Feb. 8, 2018, and a continuation of application No. PCT/US2018/017499, filed on Feb. 8, 2018, and a continuation of application No. PCT/US2018/017502, filed on Feb. 8, 2018, and a continuation of application No. PCT/US2018/017504, filed on Feb. 8, 2018, and a continuation of application No. PCT/US2018/017492, filed on Feb. 8, 2018, and a continuation of application No. PCT/US2018/017307, filed on Feb. 7, 2018.

(60) Provisional application No. 62/460,088, filed on Feb. 16, 2017, provisional application No. 62/460,076, filed on Feb. 16, 2017, provisional application No. 62/459,972, filed on Feb. 16, 2017, provisional application No. 62/460,069, filed on Feb. 16, 2017, provisional application No. 62/460,083, filed on Feb. 16, 2017, provisional application No. 62/460,047, filed on Feb. 16, 2017, provisional application No. 62/460,062, filed on Feb. 16, 2017, provisional application No. 62/460,091, filed on Feb. 16, 2017, provisional application No. 62/459,920, filed on Feb. 16, 2017, provisional application No. 62/460,075, filed on Feb. 16, 2017, provisional application No. 62/459,602, filed on Feb. 15, 2017, provisional application No. 62/459,232, filed on Feb. 15, 2017, provisional application No. 62/459,303, filed on Feb. 15, 2017, provisional application No. 62/459,577, filed on Feb. 15, 2017, provisional application No. 62/459,337, filed on Feb. 15, 2017, provisional application No. 62/459,598, filed on Feb. 15, 2017, provisional application No. 62/459,554, filed on Feb. 15, 2017, provisional application No. 62/459,496, filed on Feb. 15, 2017, provisional application No. 62/459,267, filed on Feb. 15, 2017.

(52) U.S. Cl.
CPC ..... *B01L 2200/147* (2013.01); *B01L 2300/06* (2013.01); *B01L 2300/0627* (2013.01); *B01L 2300/0809* (2013.01); *B01L 2300/12* (2013.01); *B01L 2300/1811* (2013.01); *B01L 2300/1883* (2013.01)

(58) Field of Classification Search
CPC ......... B01L 2300/0809; B01L 2300/12; B01L 2300/1811; B01L 2300/1883; B01L 7/00; B01L 9/50; B01L 2300/0893; B01L 3/50851; C12Q 1/686
USPC ....................................................... 435/278
See application file for complete search history.

(56) References Cited

U.S. PATENT DOCUMENTS

| | | | |
|---|---|---|---|
| 3,879,106 A * | 4/1975 | McCormick | G02B 21/34 |
| | | | 359/398 |
| 3,895,661 A | 7/1975 | Praglin et al. | |
| 3,925,166 A | 12/1975 | Blume | |
| 3,992,158 A | 11/1976 | Przybylowicz et al. | |
| 4,022,521 A | 5/1977 | Hall et al. | |
| 4,066,412 A | 1/1978 | Johnson et al. | |
| 4,088,448 A | 5/1978 | Lilja et al. | |
| 4,171,866 A | 10/1979 | Tolles | |
| 4,233,029 A | 11/1980 | Columbus | |
| 4,255,384 A | 3/1981 | Kitajima et al. | |
| 4,258,001 A | 3/1981 | Pierce et al. | |
| 4,329,054 A | 5/1982 | Bachalo | |
| 4,402,614 A | 9/1983 | Porath | |
| 4,427,294 A | 1/1984 | Pietro | |
| 4,430,436 A | 2/1984 | Koyama et al. | |
| 4,596,695 A | 6/1986 | Cottingham | |
| 4,745,075 A | 5/1988 | Hadfield et al. | |
| 4,806,311 A | 2/1989 | Greenquist | |
| 4,883,642 A | 11/1989 | Bisconte | |
| 4,906,439 A | 3/1990 | Grenner | |
| 4,911,782 A | 3/1990 | Brown | |
| 4,950,455 A | 8/1990 | Smith | |
| 5,002,736 A | 3/1991 | Babbitt et al. | |
| 5,039,487 A | 8/1991 | Smith | |
| 5,096,836 A | 3/1992 | Macho et al. | |
| 5,122,284 A | 6/1992 | Braynin et al. | |
| 5,132,097 A | 7/1992 | Van Deusen et al. | |
| 5,169,601 A | 12/1992 | Ohta et al. | |
| 5,188,968 A | 2/1993 | Kano et al. | |
| 5,223,219 A | 6/1993 | Subramanian et al. | |
| 5,281,540 A | 1/1994 | Merkh et al. | |
| 5,306,467 A | 4/1994 | Douglas-Hamilton et al. | |
| 5,321,975 A | 6/1994 | Wardlaw | |
| 5,362,648 A | 11/1994 | Koreyasu et al. | |
| 5,413,732 A | 5/1995 | Buhl et al. | |
| 5,427,959 A | 6/1995 | Nishimura et al. | |
| 5,431,880 A | 7/1995 | Kramer | |
| 5,591,403 A | 1/1997 | Gavin et al. | |
| 5,623,415 A | 4/1997 | O'Bryan et al. | |
| 5,753,456 A | 5/1998 | Naqui et al. | |
| 5,768,407 A | 6/1998 | Shen et al. | |
| 5,858,648 A | 1/1999 | Steel et al. | |
| 5,879,628 A | 3/1999 | Ridgeway et al. | |
| 5,888,834 A | 3/1999 | Ishikawa et al. | |
| 5,939,326 A | 8/1999 | Chupp et al. | |
| 5,948,686 A | 9/1999 | Wardlaw | |
| 6,004,821 A | 12/1999 | Levine et al. | |
| 6,016,367 A | 1/2000 | Benedetti et al. | |
| 6,017,767 A | 1/2000 | Chandler | |
| 6,022,734 A | 2/2000 | Wardlaw | |
| 6,106,778 A | 8/2000 | Oku et al. | |
| 6,180,314 B1 | 1/2001 | Berndt | |
| 6,235,536 B1 | 5/2001 | Wardlaw | |
| 6,350,613 B1 | 2/2002 | Wardlaw et al. | |
| 6,358,475 B1 | 3/2002 | Berndt | |
| 6,429,027 B1 | 8/2002 | Chee et al. | |
| 6,503,760 B2 | 1/2003 | Malmqvist et al. | |
| 6,509,085 B1 | 1/2003 | Kennedy | |
| 6,551,554 B1 | 4/2003 | Vermeiden et al. | |
| 6,623,701 B1 | 9/2003 | Fichele et al. | |
| 6,632,652 B1 | 10/2003 | Austin et al. | |
| 6,714,287 B2 | 3/2004 | Berndt | |
| 6,723,290 B1 | 4/2004 | Wardlaw | |
| 6,844,201 B2 | 1/2005 | Malmqvist et al. | |
| 6,866,823 B2 | 3/2005 | Wardlaw | |
| 6,869,570 B2 | 3/2005 | Wardlaw | |
| 6,893,850 B2 | 5/2005 | Ostuni et al. | |
| 6,921,514 B1 | 7/2005 | Vetter et al. | |
| 6,929,953 B1 | 8/2005 | Wardlaw | |
| 6,939,032 B2 | 9/2005 | Cosby et al. | |
| 7,101,341 B2 | 9/2006 | Tsukashima et al. | |
| 7,179,423 B2 | 2/2007 | Bohm et al. | |
| 7,282,367 B2 | 10/2007 | Kawamura | |
| 7,344,894 B2 * | 3/2008 | Greenstein | B01L 7/00 |
| | | | 436/518 |
| 7,393,658 B2 | 7/2008 | Carbonell et al. | |
| 7,410,617 B2 | 8/2008 | Sakamoto | |
| 7,410,807 B2 | 8/2008 | D'Aurora | |
| 7,468,160 B2 | 12/2008 | Thompson et al. | |
| 7,510,841 B2 | 3/2009 | Stuelpnagel et al. | |
| 7,510,848 B2 | 3/2009 | Hammond et al. | |

(56) References Cited

U.S. PATENT DOCUMENTS

| | | |
|---|---|---|
| 7,547,424 B2 | 6/2009 | Van Andel Res Inst |
| 7,731,901 B2 | 6/2010 | Wardlaw |
| 7,738,094 B2 | 6/2010 | Goldberg |
| 7,850,916 B2 | 12/2010 | Wardlaw |
| 7,862,773 B2 | 1/2011 | Ibrahim |
| 7,863,411 B2 | 1/2011 | Hammond et al. |
| 7,897,376 B2 | 3/2011 | Porter et al. |
| 7,901,897 B2 | 3/2011 | Stuelpnagel et al. |
| 7,903,241 B2 | 3/2011 | Wardlaw et al. |
| 7,929,121 B2 | 4/2011 | Wardlaw et al. |
| 7,929,122 B2 | 4/2011 | Wardlaw et al. |
| 7,943,093 B2 | 5/2011 | Adrien et al. |
| 7,951,599 B2 | 5/2011 | Levine et al. |
| 7,995,194 B2 | 8/2011 | Wardlaw et al. |
| 8,045,165 B2 | 10/2011 | Wardlaw et al. |
| 8,058,073 B2 | 11/2011 | Chiapperi et al. |
| 8,077,296 B2 | 12/2011 | Wardlaw et al. |
| 8,081,303 B2 | 12/2011 | Levine et al. |
| 8,133,738 B2 | 3/2012 | Levine et al. |
| 8,158,434 B2 | 4/2012 | Wardlaw |
| 8,221,985 B2 | 7/2012 | Wardlaw et al. |
| 8,241,572 B2 | 8/2012 | Wardlaw |
| 8,269,954 B2 | 9/2012 | Levine et al. |
| 8,284,384 B2 | 10/2012 | Levine et al. |
| 8,287,820 B2 | 10/2012 | Williams et al. |
| 8,310,658 B2 | 11/2012 | Wardlaw et al. |
| 8,310,659 B2 | 11/2012 | Wardlaw et al. |
| 8,319,954 B2 | 11/2012 | Wardlaw et al. |
| 8,326,008 B2 | 12/2012 | Lalpuria et al. |
| 8,338,579 B2 | 12/2012 | Adams et al. |
| 8,361,799 B2 | 1/2013 | Levine et al. |
| 8,367,012 B2 | 2/2013 | Wardlaw |
| 8,462,332 B2 | 6/2013 | Pugia et al. |
| 8,467,063 B2 | 6/2013 | Wardlaw et al. |
| 8,472,693 B2 | 6/2013 | Davis et al. |
| 8,481,282 B2 | 7/2013 | Levine et al. |
| 8,502,963 B2 | 8/2013 | Levine et al. |
| 8,513,032 B2 | 8/2013 | Jablonski et al. |
| 8,569,076 B2 | 10/2013 | Wardlaw et al. |
| 8,594,768 B2 | 11/2013 | Phillips et al. |
| 8,604,161 B2 | 12/2013 | Hammond et al. |
| 8,628,952 B2 | 1/2014 | Stuelpnagel et al. |
| 8,633,013 B2 | 1/2014 | Kaiser et al. |
| 8,638,427 B2 | 1/2014 | Wardlaw et al. |
| 8,717,673 B2 | 5/2014 | Selvin et al. |
| 8,741,630 B2 | 6/2014 | Dickinson et al. |
| 8,750,966 B2 | 6/2014 | Phillips et al. |
| 8,778,687 B2 | 7/2014 | Levine et al. |
| 8,781,203 B2 | 7/2014 | Davis et al. |
| 8,796,186 B2 | 8/2014 | Shirazi |
| 8,797,527 B2 | 8/2014 | Hukari et al. |
| 8,835,186 B2 | 9/2014 | Jablonski et al. |
| 8,837,803 B2 | 9/2014 | Wang et al. |
| 8,842,264 B2 | 9/2014 | Wardlaw et al. |
| 8,885,154 B2 | 11/2014 | Wardlaw et al. |
| 8,906,700 B2 | 12/2014 | Lim et al. |
| 8,911,815 B2 | 12/2014 | Kram et al. |
| 8,926,811 B2 | 1/2015 | Wu |
| 8,974,732 B2 | 3/2015 | Lalpuria et al. |
| 8,994,930 B2 | 3/2015 | Levine et al. |
| 9,023,641 B2 | 5/2015 | Rodriguez et al. |
| 9,044,268 B2 | 6/2015 | Phillips et al. |
| 9,046,473 B2 | 6/2015 | Levine et al. |
| 9,084,995 B2 | 7/2015 | Wardlaw |
| 9,086,408 B2 | 7/2015 | Egan et al. |
| 9,097,640 B2 | 8/2015 | Goldberg et al. |
| 9,168,530 B2 | 10/2015 | Gunter et al. |
| 9,199,233 B2 | 12/2015 | Wardlaw |
| 9,274,094 B2 | 3/2016 | Wardlaw et al. |
| 9,291,617 B2 | 3/2016 | Levine et al. |
| 9,322,835 B2 | 4/2016 | Wardlaw |
| 9,347,962 B2 | 5/2016 | Salsman |
| 9,354,159 B2 | 5/2016 | Vaartstra |
| 9,395,365 B2 | 7/2016 | Levine et al. |
| 9,469,871 B2 | 10/2016 | Bearinger et al. |
| 9,523,670 B2 | 12/2016 | Mueller et al. |
| 9,696,252 B2 | 7/2017 | Wardlaw |
| 2001/0055882 A1 | 12/2001 | Ostuni |
| 2002/0126271 A1 | 9/2002 | Berndt |
| 2002/0164820 A1 | 11/2002 | Brown |
| 2003/0068614 A1 | 4/2003 | Cima et al. |
| 2003/0107946 A1 | 6/2003 | Cosby et al. |
| 2003/0109059 A1 | 6/2003 | Adrien et al. |
| 2004/0131345 A1 | 7/2004 | Kylberg et al. |
| 2004/0156755 A1 | 8/2004 | Levine |
| 2004/0214310 A1 | 10/2004 | Parker et al. |
| 2004/0259162 A1 | 12/2004 | Kappel et al. |
| 2005/0026161 A1 | 2/2005 | Jablonski et al. |
| 2005/0032138 A1 | 2/2005 | Lathrop et al. |
| 2005/0123931 A1 | 6/2005 | Thompson et al. |
| 2005/0158880 A1 | 7/2005 | Ostuni et al. |
| 2005/0254995 A1 | 11/2005 | Sostek et al. |
| 2006/0015157 A1 | 1/2006 | Leong |
| 2006/0051253 A1 | 3/2006 | Gousepohl |
| 2006/0062440 A1 | 3/2006 | Hollars et al. |
| 2006/0062695 A1 | 3/2006 | Haab et al. |
| 2006/0090658 A1 | 5/2006 | Phillips |
| 2006/0160134 A1 | 7/2006 | Melker et al. |
| 2007/0087442 A1 | 4/2007 | Wardlaw |
| 2007/0243117 A1 | 10/2007 | Wardlaw |
| 2008/0006202 A1* | 1/2008 | Hirano ............... B01L 3/50851 |
| | | 118/60 |
| 2008/0028962 A1 | 2/2008 | Phillips et al. |
| 2008/0176757 A1* | 7/2008 | Hassibi ............... C12Q 1/6851 |
| | | 506/7 |
| 2008/0214947 A1 | 9/2008 | Hunt et al. |
| 2008/0274564 A1 | 11/2008 | D'Aurora |
| 2008/0286152 A1 | 11/2008 | Schmidt et al. |
| 2009/0211344 A1 | 8/2009 | Wang |
| 2009/0213478 A1 | 8/2009 | Kroll et al. |
| 2009/0227472 A1 | 9/2009 | Stuelpnagel et al. |
| 2009/0233329 A1 | 9/2009 | Rodriguez et al. |
| 2009/0246781 A1 | 10/2009 | Klem et al. |
| 2009/0258371 A1 | 10/2009 | Wardlaw et al. |
| 2009/0298716 A1 | 12/2009 | Stuelpnagel et al. |
| 2010/0081583 A1 | 4/2010 | Shirazi |
| 2010/0085067 A1 | 4/2010 | Gabriel et al. |
| 2010/0151593 A1 | 6/2010 | D'Aurora |
| 2010/0216248 A1 | 8/2010 | Wardlaw |
| 2010/0255605 A1 | 10/2010 | Wardlaw |
| 2010/0267127 A1* | 10/2010 | Chung ............... B01L 7/525 |
| | | 435/305.2 |
| 2010/0272345 A1 | 10/2010 | Wardlaw |
| 2010/0273244 A1 | 10/2010 | Wardlaw |
| 2010/0291562 A1 | 11/2010 | Adler |
| 2011/0009297 A1 | 1/2011 | Jones et al. |
| 2011/0206557 A1 | 8/2011 | Phan et al. |
| 2011/0294198 A1 | 12/2011 | Wardlaw |
| 2011/0305842 A1* | 12/2011 | Kram ............... G02B 21/34 |
| | | 118/58 |
| 2012/0034647 A1 | 2/2012 | Herzog et al. |
| 2012/0107799 A1 | 5/2012 | Daum |
| 2012/0108787 A1 | 5/2012 | Lue |
| 2012/0157332 A1 | 6/2012 | Kumar et al. |
| 2012/0300293 A1 | 11/2012 | Selvin et al. |
| 2013/0065788 A1 | 3/2013 | Glezer et al. |
| 2013/0102018 A1 | 4/2013 | Schentag et al. |
| 2013/0157288 A1 | 6/2013 | Kilfeather et al. |
| 2013/0209332 A1 | 8/2013 | Wardlaw |
| 2013/0265054 A1 | 10/2013 | Lowery et al. |
| 2013/0309679 A1 | 11/2013 | Ismagilov et al. |
| 2014/0315242 A1 | 10/2014 | Rodriguez et al. |
| 2014/0368631 A1 | 12/2014 | Wardlaw et al. |
| 2014/0369386 A1* | 12/2014 | Radhakrishnan ..... H01L 35/325 |
| | | 29/25.01 |
| 2015/0031039 A1 | 1/2015 | Pipper et al. |
| 2015/0036131 A1 | 2/2015 | Salsman |
| 2015/0184235 A1 | 7/2015 | Reda et al. |
| 2015/0253321 A1 | 9/2015 | Chou et al. |
| 2015/0317506 A1 | 11/2015 | Xie et al. |
| 2015/0323519 A1 | 11/2015 | Wardlaw |
| 2016/0025637 A1 | 1/2016 | Halverson et al. |
| 2016/0033496 A1 | 2/2016 | Chou et al. |
| 2016/0245797 A1 | 8/2016 | Ahmad et al. |

(56) References Cited

U.S. PATENT DOCUMENTS

| | | | |
|---|---|---|---|
| 2016/0266091 | A1 | 9/2016 | Levine et al. |
| 2017/0021356 | A1 | 1/2017 | Dority et al. |
| 2017/0038401 | A1 | 2/2017 | Holmes et al. |
| 2017/0045504 | A1 | 2/2017 | Bloom |

FOREIGN PATENT DOCUMENTS

| | | | |
|---|---|---|---|
| CN | 1299466 | | 6/2001 |
| CN | 1302229 | | 7/2001 |
| CN | 1166950 | | 9/2004 |
| CN | 1188217 | | 2/2005 |
| CN | 101522909 | A | 9/2009 |
| CN | 102027369 | | 4/2011 |
| EP | 291153 | | 6/1992 |
| EP | 261667 | | 2/1993 |
| EP | 0961110 | * | 5/1999 |
| EP | 2290100 | | 3/2011 |
| EP | 2439515 | | 4/2012 |
| EP | 2554987 | | 2/2013 |
| EP | 3026433 | | 6/2016 |
| EP | 1949310 | | 2/2019 |
| WO | 1991020009 | | 12/1991 |
| WO | 1999044743 | | 9/1999 |
| WO | 1999045385 | | 9/1999 |
| WO | 2003062920 | | 7/2003 |
| WO | 2005114145 | | 12/2005 |
| WO | 2005100539 | | 1/2006 |
| WO | 2007112332 | | 10/2007 |
| WO | 2009117652 | | 9/2009 |
| WO | 2009117664 | | 9/2009 |
| WO | 2009117678 | | 9/2009 |
| WO | 2009117682 | | 9/2009 |
| WO | 2009124186 | | 10/2009 |
| WO | 2009124190 | | 10/2009 |
| WO | 2009126800 | | 10/2009 |
| WO | 2010115026 | | 10/2010 |
| WO | 2014055559 | | 4/2014 |
| WO | 2014089468 | | 6/2014 |
| WO | 2014183049 | | 11/2014 |
| WO | 2014205576 | | 12/2014 |
| WO | 2017048871 | | 3/2017 |

OTHER PUBLICATIONS

Written Opinion for PCT/US2018/017713 established by ISA/KR, mailed on Jun. 20, 2018.

* cited by examiner

Cross-sectional view

Cross-sectional view

A.

B.

C.

D.

E.

F.

G.

ASSAY WITH RAPID TEMPERATURE CHANGE

CROSS-REFERENCE TO RELATED APPLICATIONS

This application is a § 371 national stage application of International Application PCT/US2018/018405 filed on Feb. 15, 2018, which claims the benefit of priority to U.S. Provisional Application ("USPA" hereinafter) No. 62/460,088, filed on Feb. 16, 2017, USPA No. 62/460,091, filed on Feb. 16, 2017, USPA No. 62/460,083, filed on Feb. 16, 2017, USPA No. 62/460,076, filed on Feb. 16, 2017, USPA No. 62/460,075, filed on Feb. 16, 2017, USPA No. 62/460,069, filed on Feb. 16, 2017, USPA No. 62/460,062, filed on Feb. 16, 2017, USPA No. 62/460,047, filed on Feb. 16, 2017, USPA No. 62/459,972, filed on Feb. 16, 2017, USPA No. 62/459,920, filed on Feb. 16, 2017, USPA No. 62/459,602, filed on Feb. 15, 2017, USPA No. 62/459,598, filed on Feb. 15, 2017, USPA No. 62/459,577, filed on Feb. 15, 2017, USPA No. 62/459,554, filed on Feb. 15, 2017, USPA No. 62/459,496, filed on Feb. 15, 2017, USPA No. 62/459,337, filed on Feb. 15, 2017, USPA No. 62/459,303, filed on Feb. 15, 2017, USPA No. 62/459,267, filed on Feb. 15, 2017, USPA No. 62/459,232, filed on Feb. 15, 2017, PCT Application No. PCT/US18/18108, filed on Feb. 14, 2018, PCT Application No. PCT/US18/18007, filed on Feb. 13, 2018, PCT Application No. PCT/US18/17716, filed on Feb. 9, 2018, PCT Application No. PCT/US18/17713, filed on Feb. 9, 2018, PCT Application No. PCT/US18/17712, filed on Feb. 9, 2018, PCT Application No. PCT/US18/17504, filed on Feb. 8, 2018, PCT Application No. PCT/US18/17499, filed on Feb. 8, 2018, PCT Application No. PCT/US18/17489, filed on Feb. 8, 2018, PCT Application No. PCT/US18/17492, filed on Feb. 8, 2018, PCT Application No. PCT/US18/17494, filed on Feb. 8, 2018, PCT Application No. PCT/US18/17502, filed on Feb. 8, 2018, and PCT Application No. PCT/US18/17307, filed on Feb. 7, 2018, the contents of which are relied upon and incorporated herein by reference in their entirety. The entire disclosure of any publication or patent document mentioned herein is entirely incorporated by reference.

BACKGROUND

In certain chemical, biological and/or medical assays, repeated thermal cycles and rapid and precise temperature controls need to be implemented. One particular example is the polymerase chain reaction (PCR) for amplifying pre-determined nucleotides (e.g. DNA) in one or more samples. In a PCR, the samples are repeatedly heated and cooled to specific temperatures following a pre-set thermal control cycle. In certain scenarios, it is desirable to that the temperature of the samples can be changed rapidly and uniformly.

SUMMARY OF INVENTION

The following brief summary is not intended to include all features and aspects of the present invention. The present invention provides devices, systems, and methods for rapid sample thermal cycle changes for the facilitation of reactions such as but not limited to PCR. One aspect of the present invention is to use two movable thin plates to compress a liquid sample into a uniform thin layer.

Another aspect of the present invention is to speed up sample temperature ramping speed, one of the plates of the QMAX assay is reduced to 100 um (micron) thick or less.

Another aspect of the present invention is to provide solutions to the problems associated to a very thin plate in a QMAX card under a rapid temperature change or cycling. The problem includes large deformation of the plate, the sample thickness changes, air bubble formation and other, that each of them can lead to failure of a PRC or isothermal nucleic acid amplification. Hence, it is very important, accord to the present invention, one of the solutions comprises a use of clamp with certain design to hold the two plates fixed together during the temperature changes. Certainly, the clamps in the present innovation can be used for the QMAX card that do not need to change the sample temperature.

The present invention provides the devices and methods for changing temperature of a sample quickly through making a sample into a uniform ultrathin thin over an area (or a relevant area), low thermal absorption and low thermal capacity of a sample holder, and an area heater elements.

BACKGROUND

In certain chemical, biological and/or medical assays, repeated thermal cycles and rapid and precise temperature controls need to be implemented. One particular example is the polymerase chain reaction (PCR) for amplifying pre-determined nucleotides (e.g. DNA) in one or more samples. In a PCR, the samples are repeatedly heated and cooled to specific temperatures following a pre-set thermal control cycle. In certain scenarios, it is desirable to that the temperature of the samples can be changed rapidly and uniformly.

The present invention provides devices and methods for rapid thermal cycle changes and the devices and methods herein disclosed are suitable for the facilitation of reactions such as but not limited to PCR.

BRIEF DESCRIPTION OF THE DRAWINGS

The skilled artisan will understand that the drawings, described below, are for illustration purposes only. The drawings are not intended to limit the scope of the present teachings in any way. In some cases, the drawings are not in scale. In the figures that present experimental data points, the lines that connect the data points are for guiding a viewing of the data only and have no other means.

DETAILED DESCRIPTION OF EXEMPLARY EMBODIMENTS

The following detailed description illustrates some embodiments of the invention by way of example and not by way of limitation. If any, the section headings and any subtitles used herein are for organizational purposes only and are not to be construed as limiting the subject matter described in any way. The contents under a section heading and/or subtitle are not limited to the section heading and/or subtitle, but apply to the entire description of the present invention.

The citation of any publication is for its disclosure prior to the filing date and should not be construed as an admission that the present claims are not entitled to antedate such publication by virtue of prior invention. Further, the dates of publication provided can be different from the actual publication dates which can need to be independently confirmed.

It should be noted that the Figures do not intend to show the elements in strict proportion. For clarity purposes, some elements are enlarged when illustrated in the Figures. The dimensions of the elements should be delineated from the descriptions herein provided and incorporated by reference.

QMAX-Device

The terms "CROF Card (or card)", "COF Card", "QMAX-Card", "Q-Card", "CROF device", "COF device", "QMAX-device", "CROF plates", "COF plates", and "QMAX-plates" are interchangeable, except that in some embodiments, the COF card does not comprise spacers; and the terms refer to a device that comprises a first plate and a second plate that are movable relative to each other into different configurations (including an open configuration and a closed configuration), and that comprises spacers (except some embodiments of the COF) that regulate the spacing between the plates. The term "X-plate" refers to one of the two plates in a CROF card, wherein the spacers are fixed to this plate. More descriptions of the COF Card, CROF Card, and X-plate are described in the provisional application Ser. No. 62/456,065, filed on Feb. 7, 2017, which is incorporated herein in its entirety for all purposes.

Figure 1:
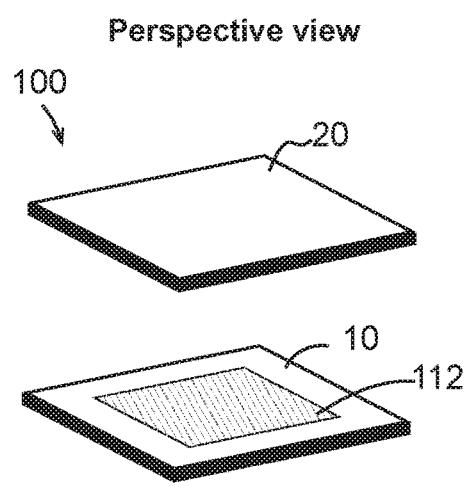
FIG. 1 shows perspective and sectional views of an embodiment of the device of the present invention; panel (A) illustrates an embodiment of the device in an open configuration; panel (B) illustrates an embodiment of the device when the sample unit is in a closed configuration, where the temperature of a sample that is compressed into a thin layer between two plates is rapidly changed by a radiation source that is positioned to project electromagnetic waves onto the sample.
Figure 1:
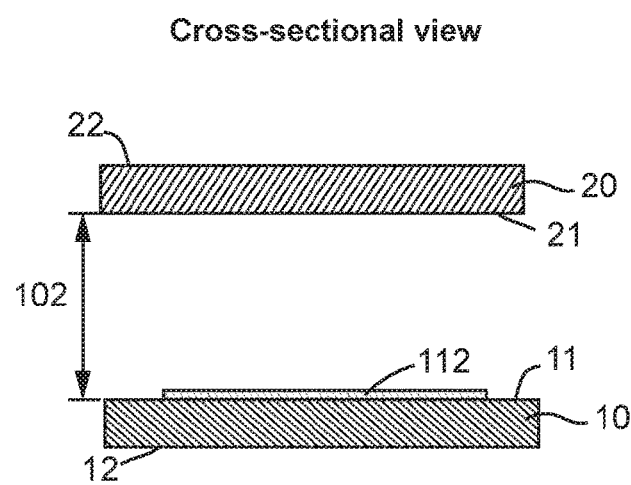
Figure 1:
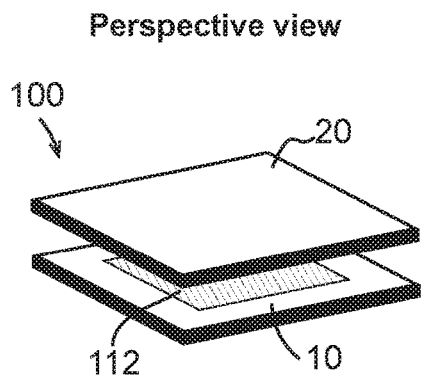
Figure 1:
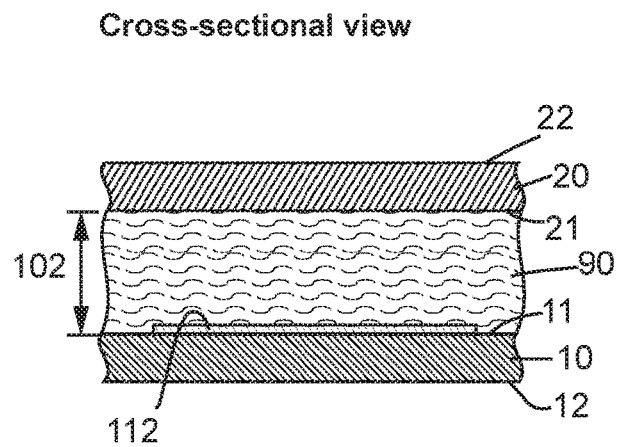

FIG. 1 shows perspective and sectional views of an embodiment of the device of the present invention. Panel (A) illustrates the device (also termed "sample unit" of the system) 100 in an open configuration. As shown in panel (A), the sample unit 100 comprises a first plate 10, a second plate 20, and a spacing mechanism (not shown). The first plate 10 and second plate 20 respectively comprise an outer surface (11 and 21, respectively) and an inner surface (12 and 22, respectively). Each inner surface has a sample contact area (not indicated) for contacting a fluidic sample to be processed and/or analyzed by the device.

The first plate 10 and the second plate 20 are movable relative to each other into different configurations. One of the configurations is the open configuration, in which, as shown in FIG. 1 panel (A), the first plate 10 and the second plate 20 are partially or entirely separated apart, and the spacing between the first plate 10 and the second plate 20 (i.e. the distance between the first plate inner surface 11 and the second plate inner surface 21) is not regulated by the spacing mechanism. The open configuration allows a sample to be deposited on the first plate, the second plate, or both, in the sample contact area.

As shown in panel (A) of FIG. 1, the first plate 10 further comprises a radiation absorbing layer 112 in the sample contact area. It is also possible that the second plate 20 alternatively or additionally comprise the radiation absorbing layer 112. is In some embodiments, the radiation absorbing layer 112 is configured to efficiently absorb radiation (e.g. electromagnetic waves) shed on it. The absorption percentage is 50% or more, 60% or more, 70% or more, 80% or more, 90% or more, 95% or more, 99% or more, 100% or less, 85% or less, 75% or less, 65% or less, or 55% or less, or in a range between any of the two values. The radiation absorbing layer 112 is further configured to convert at least a substantial portion of the absorbed radiation energy into heat (thermal energy). For example, the radiation absorbing layer 112 is configured to emit radiation in the form of heat after absorbing the energy from electromagnetic waves. The term "substantial portion" or "substantially" as used herein refers to a percentage that is 50% or more, 60% or more, 70% or more, 80% or more, 90% or more, 95% or more, 99% or more, 99% or more, or 99.9% or more.

In some embodiments, the radiation absorbing layer 112 comprise materials/structures, such as, but not limited to, metallic plasmonic surface, metamaterials, black silicon, graphite, carbon nanotube, silicon sandwich, graphene, superlattice, plasmonic materials, any material/structure that is capable of efficiently absorbing the electromagnetic wave and converting the absorbed energy into thermal energy, and any combination thereof. In certain embodiments, the radiation absorbing layer 112 comprise carbon nanotube.

In some embodiments, the radiation absorbing layer comprise a dot-coupled-dots-on-pillar antenna (D2PA) array, such as, but not limited to the D2PA array described in U.S. Provisional Patent Application No. 61/347,178, which was filed on May 21, 2010, U.S. Provisional Patent Application 61/622,226, which was filed on Apr. 10, 2012, U.S. Provisional Patent Application No. 61/801,424, which was filed on Mar. 15, 2013, U.S. Provisional Patent Application No. 61/801,096, which was filed on Mar. 15, 2013, U.S. Provisional Patent Application No. 61/801,933, which was filed on Mar. 15, 2013, U.S. Provisional Patent Application No. 61/794,317, which was filed on Mar. 15, 2013, U.S. Provisional Patent Application No. 62/090,299, which was filed on Dec. 10, 2014, U.S. Provisional Patent Application No. 61/708,314, which was filed on Oct. 1, 2012, PCT Application No. PCT/US2011/037455, which was filed on May 20, 2011, PCT Application No. PCT/US2013/032347, which was filed on Mar. 15, 2013, PCT Application No. PCT/US2014/029979, which was filed on Mar. 15, 2014, PCT Application No. PCT/US2014/028417, which was filed on Mar. 14, 2014, PCT Application No. PCT/US2014/030108, which was filed on Mar. 16, 2014, PCT Application No. PCT/US2013/062923, which was filed on Oct. 1, 2013, U.S. patent application Ser. No. 13/699,270, which was filed on Jun. 13, 2013, U.S. patent application Ser. No. 14/459,239, which was filed on Aug. 13, 2014, U.S. patent application Ser. No. 14/871,678, which was filed on Sep. 30, 2015, U.S. patent application Ser. No. 13/838,600, which was filed on Mar. 15, 2013, U.S. patent application Ser. No. 14/459,251, which was filed on Aug. 13, 2014, U.S. patent application Ser. No. 14/668,750, which was filed on Mar. 25, 2015, U.S. patent application Ser. No. 14/775,634, which was filed on Sep. 11, 2015, U.S. patent application Ser. No. 14/775,638, which was filed on Sep. 11, 2015, U.S. patent application Ser. No. 14/852,412, which was filed on Mar. 16, 2014, U.S. patent application Ser. No. 14/964,394, which was filed on Dec. 9, 2015, U.S. patent application Ser. No. 14/431,266, which was filed on Oct. 5, 2015, the complete disclosures of which are hereby incorporated by reference for all purposes.

Panel (B) of FIG. 1 shows perspective and sectional views of the sample unit 100 when it is in a closed configuration. The sectional view illustrates part of the device without showing the entirety of the sample unit 100 or the spacing mechanism. As shown in panel (B), the sample unit 100 comprises a first plate 10, a second plate 20, and a spacing mechanism (not shown).

In FIG. 1 panel (B), the first plate 10 and the second plate 20 are in a closed configuration. In the closed configuration, the inner surfaces of the two plates 11 and 21 face each other, and the spacing between the two plates 102 is regulated by the spacing mechanism. Consequently, as shown in the figure, the two plates compress a fluidic sample 90 that is deposited on one or both of the plates into a layer, and the thickness of the layer is regulated by the spacing mechanism (not illustrated).

NN1 A device for rapidly changing temperature of a thin fluidic sample layer, comprising: a first plate, and a second plate, wherein:
  i. each of the plates comprises, on its respective surface, a sample contact area for contacting a fluidic sample; and
  ii. the plates have a configuration for rapidly changing temperature of the sample, in which:
    a. the sample contact areas face each other and are significant parallel,
    b. the average spacing between the contact areas is equal to or less than 200 microns,
    c. the two plates regulate (or confine) at least part of the sample into a layer of highly uniform thickness and substantially stagnant relative to the plates,
    d. the radiation absorbing layer is near the at least part of the sample of uniform thickness,
    e. the area of the at least part of the sample and the radiation absorbing layer are substantially larger than the uniform thickness.

In some embodiments of the present invention there are spacers between the two plates.

In some embodiments, there is an "evaporation-prevention ring" outside of the liquid area (e.g. sample area) that prevents or reduces the vapor of the liquid escape the card, during a heating.

In some embodiments, there is clamp outside of the QMAX-card to fix the QMAX card in its closed configuration during a heating.

In some embodiments, in order to achieve fast and uniform thermal change in a sample, the sample is compressed into a thin layer. The thickness of the layer is 500 □m or less, 200 □m or less, 100 □m or less, 50 □m or less, 20 □m or less, 10 □m or less, 5 □m or less, 2 □m or less, 1 □m or less, 500 nm or more, 1.5 □m or more, 2.5 □m or more, 7.5 □m or more, 15 □m or more, 30 □m or more, 75 □m or more, 150 □m or more, or 250 □m or more. The small thickness of the sample layer results in a faster diffusion of reagents and/or faster transduction of heat. In some embodiments, the two plates are compressed by an imprecise pressing force, which is neither set to a precise level nor substantially uniform. In certain embodiments, the two plates are pressed directly by a human hand.

In some embodiments, the QMAX card, including the plates and spacer, is made of the material with low thermal conductivity to reduce the heat absorption by card self.

In some embodiments, there is clamp outside of the QMAX-card to fix the QMAX card in its closed configuration during a heating.

wherein the clamp is also made of the material with low thermal conductivity to reduce the heat absorption by card self.

The term "cover" means that the areas on the plate that are in thermal conduction contact with a clamp. For example, the clamp covers some of the surface of QMAX card in a closed configuration means that the clamp has a thermal conduction contact with a part of the plate surface a QMAX card.

The term "seal" by a clamp means that that the clamp prevents or reduce, in a closed configuration of the plates, at least a part of the sample flow from one location of the plate to the other location of the plate.

For example, a clamp can be configured to seal a part of the sample or the entire sample.

The term "clamp" refers to a device comprising two elements that insert a compress force to holds a third element or more elements to together. For example, a clamp holds two plates together.

wherein these materials contain but not limit to polymers (e.g. plastics) or amorphous organic materials. The polymer materials include, not limited to, acrylate polymers, vinyl polymers, olefin polymers, cellulosic polymers, noncellulosic polymers, polyester polymers, Nylon, cyclic olefin copolymer (COC), poly(methyl methacrylate) (PMMA), polycarbonate (PC), cyclic olefin polymer (COP), liquid crystalline polymer (LCP), polyamide (PA), polyethylene (PE), polyimide (PI), polypropylene (PP), poly(phenylene ether) (PPE), polystyrene (PS), polyoxymethylene (POM), polyether ether ketone (PEEK), polyether sulfone (PES), poly(ethylene phthalate) (PET), polytetrafluoroethylene (PTFE), polyvinyl chloride (PVC), polyvinylidene fluoride (PVDF), polybutylene terephthalate (PBT), fluorinated ethylene propylene (FEP), perfluoroalkoxyalkane (PFA), polydimethylsiloxane (PDMS), rubbers, or any combinations of thereof.

wherein these materials contain but not limit to inorganic materials including dielectric materials of silicon oxide, porcelain, orcelain (ceramic), mica, glass, oxides of various metals, etc.

wherein these materials contain but not limit to inorganic compounds including aluminium oxide, aluminium chloride, cadmium sulfide, gallium nitride, gold chlorid, indium arsenide, lithium borohydride, silver bromide, sodium chloride, etc.

wherein these materials contain liquid including but not limit to water, ethane, methane, oil, benzene, Hexane, heptane, silicone oil, polychlorinated biphenyls, liquid air, liquid oxygen, liquid nitrogen etc.

wherein these materials contain gas including but not limit to air, argon, helium, nitrogen, oxygen, carbon dioxide, etc.

wherein the materials is the combination of above materials.

In some embodiments, the average thickness for at least one of the plates is in the range of 1 to 1000 μm, 10 to 900 μm, 20 to 800 μm, 25 to 700 μm, 25 to 800 μm, 25 to 600 μm, 25 to 500 μm, 25 to 400 μm, 25 to 300 μm, 25 to 200 μm, 30 to 200 μm, 35 to 200 μm, 40 to 200 μm, 45 to 200 μm, or 50 to 200 μm.

In some embodiments, the average thickness for at least one of the plates is in the range of 50 to 75 µm, 75 to 100 µm, 100 to 125 µm, 125 to 150 µm, 150 to 175 µm, or 175 to 200 µm.

In some embodiments, the average thickness for at least one of the plates is about 50 µm, about 75 µm, about 100 µm, about 125 µm, about 150 µm, about 175 µm, or about 200 µm.

The height of the spacers is selected by a desired regulated spacing between the plates and/or a regulated final sample thickness and the residue sample thickness. The spacer height (the predetermined spacer height), the spacing between the plates, and/or sample thickness is 3 nm or less, 10 nm or less, 50 nm or less, 100 nm or less, 200 nm or less, 500 nm or less, 800 nm or less, 1000 nm or less, 1 µm or less, 2 µm or less, 3 µm or less, 5 µm or less, 10 µm or less, 20 µm or less, 30 µm or less, 50 µm or less, 100 µm or less, 150 µm or less, 200 µm or less, 300 µm or less, 500 µm or less, 800 µm or less, 1 mm or less, 2 mm or less, 4 mm or less, or in a range between any two of the values.

The spacer height, the spacing between the plates, and/or sample thickness is between 1 nm to 100 nm in one preferred embodiment, 100 nm to 500 nm in another preferred embodiment, 500 nm to 1000 nm in a separate preferred embodiment, 1 µm (i.e. 1000 nm) to 2 µm in another preferred embodiment, 2 µm to 3 µm in a separate preferred embodiment, 3 µm to 5 µm in another preferred embodiment, 5 µm to 10 µm in a separate preferred embodiment, and 10 µm to 50 µm in another preferred embodiment, 50 µm to 100 µm in a separate preferred embodiment.

In some embodiments, the QMAX device is fully transparent or partially transparent to reduce the heat absorption by card self. wherein the transparence is above 30%, 40%, 50%, 60%, 70%, 80%, 90%, 100%, or a range between any two of the values.

In some embodiments, the QMAX device is partially reflective to reduce the heat absorption by card self wherein the reflectance of the surface is above 30%, 40%, 50%, 60%, 70%, 80%, 90%, 100%, or a range between any two of the values.

In some embodiments, the QMAX and clamp is coated heat insulator layer to reduce the heat absorption by card self. Wherein the heat insulator layer contains materials including the low thermal conductivity material above.

In some embodiments, the clamp cover and seal all the QMAX card in close configuration.

In some embodiments, the clamp cover some of the surface of QMAX card in close configuration.

In some embodiments, the clamp has a window which is transparent to allow the light go inside the QMAX card and out from the QMAX card.

In some embodiments, the clamp is fully transparent to allow the light go inside the QMAX card and out from the QMAX card.

wherein the transparence of the clamp is above 30%, 40%, 50%, 60%, 70%, 80%, 90%, 100%, or a range between any two of the values.

In some embodiments, there is air or liquid between the clamp and QMAX device in close configuration.

wherein the liquid including but not limit to water, ethane, methane, oil, benzene, Hexane, heptane, silicone oil, polychlorinated biphenyls, liquid air, liquid oxygen, liquid nitrogen etc.

wherein the gas including but not limit to air, argon, helium, nitrogen, oxygen, carbon dioxide, etc.

In some embodiments, after close the clamp, the pressure on QMAX card surface applied by the clamp is 0.01 kg/cm2, 0.1 kg/cm2, 0.5 kg/cm2, 1 kg/cm2, 2 kg/cm2, kg/cm2, 5 kg/cm2, 10 kg/cm2, 20 kg/cm2, 30 kg/cm2, 40 kg/cm2, 50 kg/cm2, 60 kg/cm2, 100 kg/cm2, 150 kg/cm2, 200 kg/cm2, or a range between any two of the values; and a preferred range of 0.1 kg/cm2 to 0.5 kg/cm2, 0.5 kg/cm2 to 1 kg/cm2, 1 kg/cm2 to 5 kg/cm2, 5 kg/cm2 to 10 kg/cm2 (Pressure).

As shown in the cross-sectional views of the device in FIG. 1, the radiation absorbing layer 112 spans across the sample contact area. It should be noted, however, it is also possible that the lateral area of the radiation absorbing layer occupy only a portion of the sample contact area at a percentage about 1% or more, 5% or more, 10% or more, 20% or more, 50% or more, 80% or more, 90% or more, 95% or more, 99% or more, 85% or less, 75% or less, 55% or less, 40% or less, 25% or less, 8% or less, 2.5% or less. In some embodiments, in order to facilitate the temperature change of the sample, in some embodiments the lateral area of the radiation absorbing layer is configured so that the sample 90 receive the thermal radiation from the radiation absorbing layer 112 substantially uniformly across the lateral dimension of the sample 90 over the sample contact area.

In some embodiments, the radiation absorbing area is 10%, 30%, 40%, 50%, 60%, 70%, 80%, 90%, 100% the total plate area, or a range between any two of the values.

In some embodiments, the radiation absorbing layer 112 have a thickness of 10 nm or more, 20 nm or more, 50 nm or more, 100 nm or more, 200 nm or more, 500 nm or more, 1 □m or more, 2 □m or more, 5 □m or more, 10 □m or more, 20 □m or more, 50 □m or more, 100 □m or more, 75 □m or less, 40 □m or less, 15 □m or less, 7.5 □m or less, 4 □m or less, 1.5 □m or less, 750 nm or less, 400 nm or less, 150 nm or less, 75 nm or less, 40 nm or less, or 15 nm or less, or in a range between any of the two values. In certain embodiments, the radiation absorbing layer 112 have thickness of 100 nm or less.

In some embodiments, the area of the sample layer and the radiation absorbing layer 112 is substantially larger than the uniform thickness. Here, the term "substantially larger" means that the general diameter or diagonal distance of the sample layer and/or the radiation absorbing layer is at least 10 time, 15 times, 20 time, 25 times, 30 time, 35 times, 40 time, 45 times, 50 time, 55 times, 60 time, 65 times, 70 time, 75 times, 80 time, 85 times, 90 times, 95 times, 100 time, 150 times, 200 time, 250 times, 300 time, 350 times, 400 time, 450 time, 500 time, 550 times, 600 time, 650 times, 700 time, 750 times, 800 time, 850 time, 900 time, 950 times, 1000 time, 1500 times, 2000 time, 2500 times, 3000 time, 3500 times, 4000 time, 4500 time, or 5000 time, or in a range between any of the two values.

System Including QMAX Device

Figure 2:
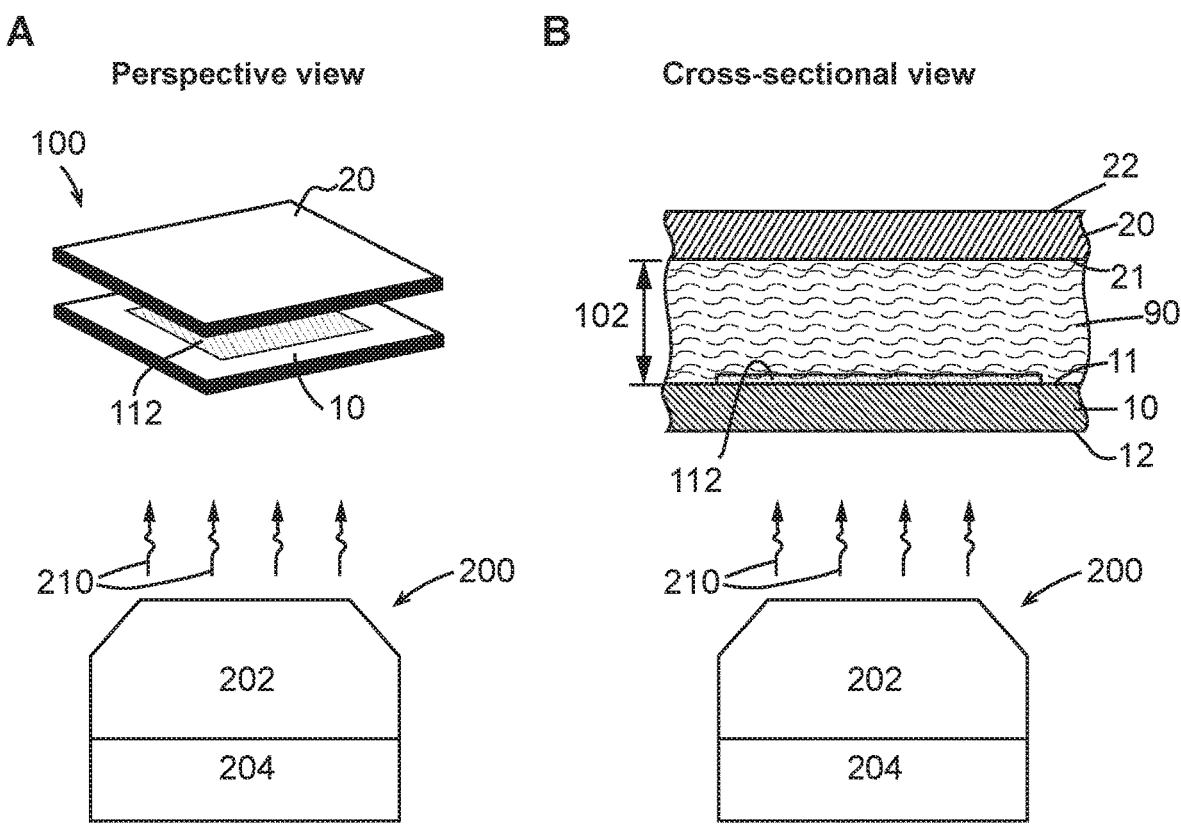
FIG. 2 shows perspective and sectional views of an embodiment of the system of the present invention; panel (A) illustrates the perspective view of the system when the device (sample unit of the system) is in an open configuration; panel (B) illustrates the sectional view of the system when the sample unit is in a closed configuration.

FIG. 2 shows perspective and sectional views of an embodiment of the system of the present invention. As shown in panels (A) and (B), the system comprise a sample unit 100 and a thermal control unit 200; the sample unit 100 comprise a first plate 10, a second plate 20, and a spacing mechanism (not shown); the thermal control unit 200 comprise a radiation source 202 and controller 204. Panels (A) and (B) of FIG. 2 illustrate the perspective view and sectional view of the system when the sample unit 100 of the system is in a closed configuration.

As shown in panel (B) of FIG. 1, the thermal control unit 200 comprise a radiation source 202 and controller 204. In some embodiments, the thermal control unit 200 provide the energy in the form of electromagnetic waves for temperature change of the sample.

Referring to both panels (A) and (B) of FIG. 2, the radiation source 202 is configured to project an electromagnetic wave 210 to the radiation absorbing layer 112 of the sample unit 100, which is configured to absorb the electromagnetic wave 210 and convert a substantial portion of the electromagnetic wave 210 into heat, resulting in thermal radiation that elevate the temperature of a portion of the sample 90 that is in proximity of the radiation absorbing layer 112. In other words, the coupling of the radiation source 202 and the radiation absorbing layer 112 is configured to generate the thermal energy that is needed to facilitate the temperature change of the sample 90.

In some embodiments, the radiation from the radiation source 202 comprises radio waves, microwaves, infrared waves, visible light, ultraviolet waves, X-rays, gamma rays, or thermal radiation, or any combination thereof. In some embodiments, the radiation absorbing layer 112 has a preferred range of light wavelength at which the radiation absorbing layer 112 has the highest absorption efficiency. In some embodiments, the radiation source 202 is configured to project the electromagnetic wave at a wavelength range within, overlapping with, or enclosing the preferred wavelength range of the radiation absorbing layer 112. In other embodiments, in order to facilitate the temperature change, the wavelength is rationally designed away from the preferred wavelength of the radiation absorbing layer.

In some embodiments, the radiation source 202 comprises a laser source providing a laser light within a narrow wavelength range. In other embodiments, the radiation source 202 comprises a LED (light-emitting diode) of a plurality thereof.

Referring to panels (A) and (B) of FIG. 2, the controller 204 is configured to control the electromagnetic wave 210 projected from the radiation source 202 for the temperature change of the sample. The parameters of the electromagnetic wave 210 that the controller 204 controls include, but are not limited to, the presence, intensity, wavelength, incident angle, and any combination thereof. In some embodiments, the controller is operated manually, for instance, it is as simple as a manual switch that controls the on and off of the radiation source, and therefore the presence of the electromagnetic wave projected from the radiation source. In other embodiments, the controller includes hardware and software that are configured to control the electromagnetic wave automatically according to one or a plurality of pre-determined programs.

In some embodiments, the pre-determined program refers to a schedule in which the parameter(s) (e.g. presence, intensity, and/or wavelength) of the electromagnetic wave 210 is/are set to pre-determined levels for respective pre-determined periods of time. In other embodiments, the pre-determined program refers to a schedule in which the temperature of the sample 90 is set to pre-determined levels for respective pre-determined periods of time and the time periods for the change of the sample temperature from one pre-determined level to another pre-determined level are also set respectively. In some embodiments, the controller 204 is configured to be programmable, which means the controller 204 comprises hardware and software that are configured to receive and carry out pre-determined programs for the system that are delivered by the operator of the system.

The thermal cycler system and associated methods of the present invention is used to facilitate a chemical, biological or medical assay or reaction. In some embodiments, the reaction requires temperature changes. In some embodiments, the reaction requires or prefers rapid temperature change in order to avoid non-specific reaction and/or reduce wait time. In certain embodiments, the system and methods of the present invention is used to facilitate a reaction that requires cyclical temperature changes for amplification of a nucleotide in a fluidic sample; such reactions includes but not is limited to polymerase chain reaction (PCR). The descriptions below use PCR as an example to illustrate the capability and utilization of the thermal cycler system and method of the present invention. It is should be noted, however, some embodiments of the device, systems and method herein described also apply to other assays and/or reactions that require temperature control and change.

Referring to panel (B) of FIG. 2, in some embodiments, the sample 90 is a pre-mixed reaction medium for polymerase chain reaction (PCR). For example, in certain embodiments, the reaction medium includes components such as but not limited to: DNA template, two primers, DNA polymerase (e.g. Taq polymerase), deoxynucleoside triphosphates (dNTPs), bivalent cations (e.g. $Mg^{2+}$), monovalent cation (e.g. $K^+$), and buffer solution. The specific components, the concentrations of each component, and the overall volume varies according to rational design of the reaction.

In some embodiments, the PCR assay requires a number of changes/alterations in sample temperature between the following steps: (i) the optional initialization step, which requires heating the sample to 92-98° C.; (2) the denaturation step, which requires heating the sample to 92-98° C.; (3) the annealing step, which requires lowering the sample temperature to 50-65° C.; (4) extension (or elongation) step, which requires heating the sample to 75-80° C.; (5) repeating steps (2)-(4) for about 20-40 times; and (6) completion of the assay and lowering the temperature of the sample to ambient temperature (e.g. room temperature) or cooling to about 4° C. The specific temperature and the specific time period for each step varies and depends on a number of factors, including but not limited to length of the target sequence, length of the primers, the cation concentrations, and/or the GC percentage.

The thermal cycler system of the present invention provides rapid temperature change for the PCR assay. For example, referring to panels (A) and (B) of FIG. 1 and panel (B) of FIG. 2, in some embodiments, the sample 90 (e.g. pre-mixed reaction medium) is added to one or both of the plates 10 and 20 in the open configuration and the plates is switched to the closed configuration to compress the sample 90 into a thin layer which has a thickness 102 that is regulated by a spacing mechanism (not shown); the radiation source 202 projects a electromagnetic wave 210 to the first plate 10 (e.g. specifically to the radiation absorbing layer 112); the radiation absorbing layer 112 is configured to absorb the electromagnetic wave 210 and convert at least a substantial portion of said electromagnetic wave 210 into heat, which increases the temperature of the sample; the removal of the electromagnetic wave 210 results in a temperature decrease in the sample 90.

In some embodiments, by projecting a electromagnetic wave 210 to the radiation absorbing layer 112 or increasing the intensity of the electromagnetic wave, the thermal cycler systems provide rapid heating (increase temperature) for any or all of the initialization step, the denaturation step and/or the extension/elongation step; in some embodiments, with the removal of the electromagnetic wave projected from the radiation source 202 or the decrease of the intensity of the electromagnetic wave, the cooling to the annealing step and/or the final cooling step is achieved with rapid speed. In some embodiments, the electromagnetic wave 210 or an increase of the intensity of the electromagnetic wave 210 creates an ascending temperature ramp rate of at least 50° C./s, 45° C./s, 40° C./s, 35° C./s, 30° C./s, 25° C./s, 20° C./s, 18° C./s, 16° C./s, 14° C./s, 12° C./s, 10° C./s, 9° C./s, 8° C./s, 7° C./s, 6° C./s, 5° C./s, 4° C./s, 3° C./s, or 2° C./s, or in a range between any of the two values. In certain embodiments, the average ascending temperature ramp rate in a PCR assay is 10° C./s or more. In some embodiments, the removal of the electromagnetic wave 210 or a reduction of the intensity of the electromagnetic wave 210 results in a descending temperature ramp rate of at least 50° C./s, 45° C./s, 40° C./s, 35° C./s, 30° C./s, 25° C./s, 20° C./s, 18° C./s, 16° C./s, 14° C./s, 12° C./s, 10° C./s, 9° C./s, 8° C./s, 7° C./s, 6° C./s, 5° C./s, 4° C./s, 3° C./s, or 2° C./s, or in a range between any of the two values. In certain embodiments, the average descending temperature ramp rate in a PCR assay is 5° C./s or more. As used here, the term "ramp rate" refers to the speed of temperature change between two pre-set temperatures. In some embodiments, the average ascending or descending temperature to each step is different.

During a PCR, within any step after the target temperature has been reached, the sample needs to be maintained at the target temperature for a certain period of time. The thermal cycler system of the present invention provides the temperature maintenance function by (1) adjusting the intensity of the electromagnetic wave 210, lowering it if the temperature has been raised to the target or increasing it if the temperature has been decreased to the target, and/or (2) keep the target temperature by balancing the heat provided to the sample and the heat removed from the sample.

Figure 3:
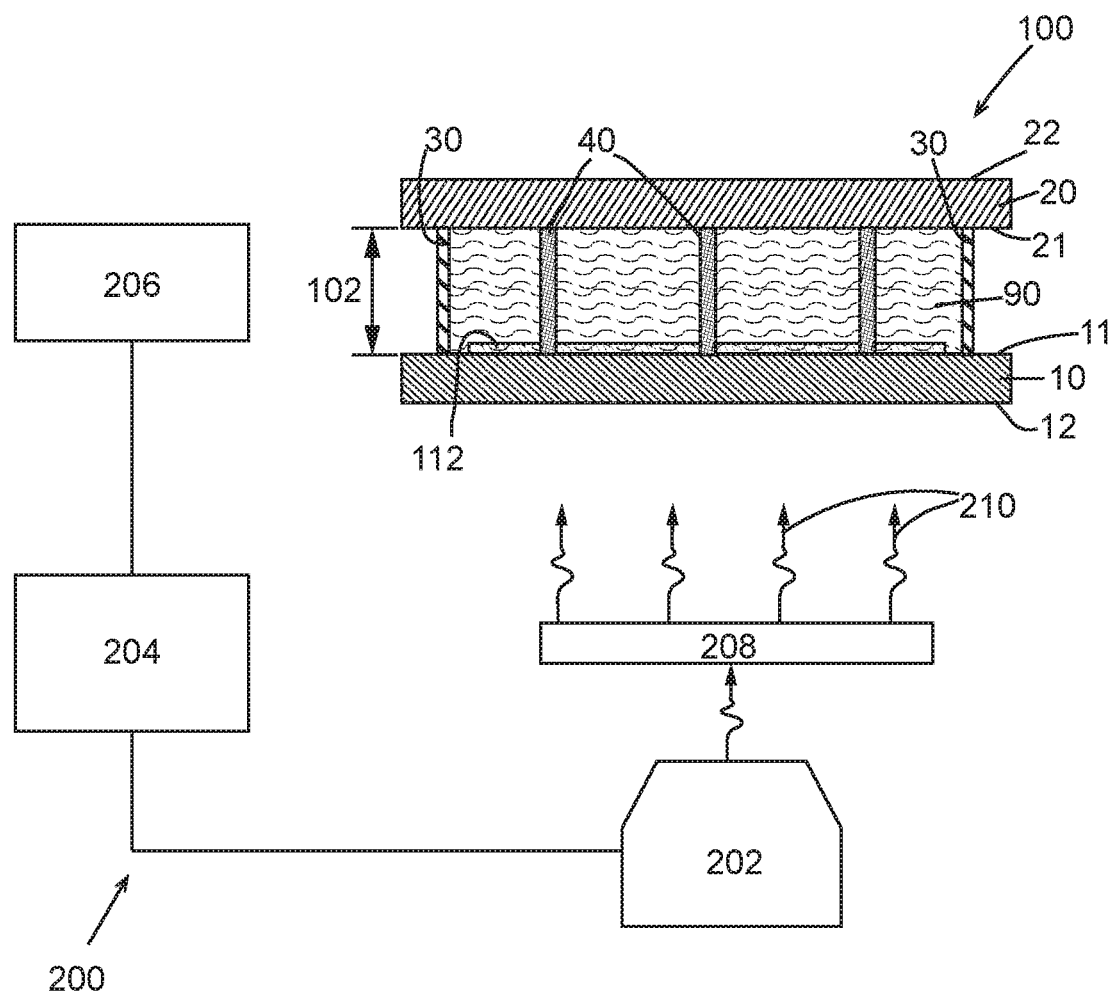
FIG. 3 shows a sectional view of an embodiment of the system of the present invention, demonstrating the system and showing additional elements that facilitate temperature change and control.

FIG. 3 shows a sectional view of an embodiment of the present invention, demonstrating the thermal cycler system and showing additional elements that facilitates temperature change and control. As shown in FIG. 2, the thermal cycler system comprises a sample unit 100 and a thermal control unit 200. The sample unit 100 comprises a first plate 10, a second plate 20, a spacing mechanism 40, and a sealing element 30; the thermal control unit 200 comprises a radiation source 202, a controller 204, a thermometer 206, and an expander 208.

FIG. 3 shows the sample unit 100 in a closed configuration, in which the inner surfaces 11 and 21 of the first and second plates 10 and 20 face each other and the spacing 102 between the two plates are regulated by a spacing mechanism 40. If a sample 90 has been deposited on one or both of the plates in the open configuration, when switching to the closed configuration, the first plate 10 and the second plate 20 are pressed by a human hand or other mechanisms, the sample 90 is thus compressed by the two plates into a thin layer. In some embodiments, the thickness of the layer is uniform and the same as the spacing 102 between the two plates. In certain embodiments, the spacing 102 (and thus the thickness of the sample layer) is regulated by the spacing mechanism 40. In some embodiments, the spacing mechanism comprises an enclosed spacer that is fixed to one of the plates. In some embodiments, the spacing mechanism 40 comprises a plurality of pillar shaped spacers that are fixed to one or both of the plates. Here the term "fixed" means that the spacer(s) is attached to a plate and the attachment is maintained during at least a use of the plate.

In some embodiments, the sample unit 10 is a compressed regulated open flow (CROF, also known as QMAX) device, such as but not limited to the CROF device described in U.S. Provisional Patent Application No. 62/202,989, which was filed on Aug. 10, 2015, U.S. Provisional Patent Application No. 62/218,455, which was filed on Sep. 14, 2015, U.S. Provisional Patent Application No. 62/293,188, which was filed on Feb. 9, 2016, U.S. Provisional Patent Application No. 62/305,123, which was filed on Mar. 8, 2016, U.S. Provisional Patent Application No. 62/369,181, which was filed on Jul. 31, 2016, U.S. Provisional Patent Application No. 62/394,753, which was filed on Sep. 15, 2016, PCT Application (designating U.S.) No. PCT/US2016/045437, which was filed on Aug. 10, 2016, PCT Application (designating U.S.) No. PCT/US2016/051775, which was filed on Sep. 14, 2016, PCT Application (designating U.S.) No. PCT/US2016/051794, which was filed on Sep. 15, 2016, and PCT Application (designating U.S.) No. PCT/US2016/054025, which was filed on Sep. 27, 2016, the complete disclosures of which are hereby incorporated by reference for all purposes.

In some embodiments, the sample unit 100 comprises a sealing element 30 that is configured to seal the spacing 102 between the first plate 10 and second plate 20 outside the medium contact area at the closed configuration. In certain embodiments, the sealing element 30 encloses the sample 90 within a certain area (e.g. the sample receiving area) so that the overall lateral area of the sample 90 is well defined and measurable. In certain embodiments, the sealing element 30 improves the uniformity of the sample 90, especially the thickness of the sample layer.

In some embodiments, the sealing element 30 comprises an adhesive applied between the first plate 10 and second plate 20 at the closed configuration. The adhesive is selective from materials such as but not limited to: starch, dextrin, gelatine, asphalt, bitumin, polyisoprenenatural rubber, resin, shellac, cellulose and its derivatives, vinyl derivatives, acrylic derivatives, reactive acrylic bases, polychloroprene, styrene-butadiene, sytyrene-diene-styrene, polyisobutylene, acrylonitrile-butadiene, polyurethane, polysulfide, silicone, aldehyde condensation resins, epoxide resins, amine base resins, polyester resins, polyolefin polymers, soluble silicates, phosphate cements, or any other adhesive material, or any combination thereof. In some embodiments, the adhesive is drying adhesive, pressure-sensitive adhesive, contact adhesive, hot adhesive, or one-part or multi-part reactive adhesive, or any combination thereof In some embodiments, the glue is natural adhesive or synthetic adhesive, or from any other origin, or any combination thereof. In some embodiments, the adhesive is spontaneous-cured, heat-cured, UV-cured, or cured by any other treatment, or any combination thereof.

In some embodiments, the sealing element 30 comprises an enclosed spacer (well). For example, the enclosed spacer has a circular shape (or any other enclosed shape) from a top view and encircle the sample 90, essentially restricting the sample 90 together with the first plate 10 and the second plate 20. In certain embodiments, the enclosed spacer (well) also function as the spacing mechanism 40. In such embodiments, the enclosed spacer seals the lateral boundary of the sample 90 as well as regulate the thickness of the sample layer.

In some embodiments, the controller 204 is configured to adjust the temperature of the sample to facilitate an assay and/or reaction involving the sample 90 according to a pre-determined program. In some embodiments, the assay and/or reaction is a PCR. In certain embodiments, the controller 204 is configured to control the presence, intensity, and/or frequency of the electromagnetic wave from the radiation source 206.

As shown in FIG. 3, in some embodiments the thermal control unit 200 comprises a thermometer 206. In some embodiments, the thermometer 206 provides a monitoring and/or feedback mechanism to control/monitor/adjust the temperature of the sample 90. For example, in some embodiments the thermometer 206 is configured to measure the temperature at or in proximity of the sample contact area. In certain embodiments, the thermometer 206 is configured to directly measure the temperature of the sample 90. In some embodiments, the thermometer 206 is selected from the group consisting of: fiber optical thermometer, infrared thermometer, fluidic crystal thermometer, pyrometer, quartz thermometer, silicon bandgap temperature sensor, temperature strip, thermistor, and thermocouple. In certain embodiments, the thermometer 206 is an infrared thermometer.

In some embodiments, the thermometer 206 is configured to send signals to the controller 204. Such signals comprise information related to the temperature of the sample 90 so that the controller 204 makes corresponding changes. For example, during a PCR, for the denaturation step the target temperature is set for 95° C.; after measurement, the thermometer sends a signal to the controller 204, indicating that the measured temperature of the sample 90 is actually 94.8° C.; the controller 204 thus alters the output the radiation source 202, which projects a electromagnetic wave or adjust particular parameters (e.g. intensity or frequency) of an existing electromagnetic wave so that the temperature of the sample 90 is increased to 95° C. Such measurement-signaling-adjustment loop is applied to any step in any reaction/assay.

As shown in FIG. 3, the thermal control unit 200 comprises a beam expander 208, which is configured to expand the electromagnetic wave from the radiation source 202 from a smaller diameter to a larger diameter. In some embodiments, the electromagnetic wave projected from the radiation source 202 is sufficient to cover the entire sample contact area; in some embodiments however, it is necessary to expand the covered area of the electromagnetic wave projected directed from the radiation source 202 to produce an expanded electromagnetic wave 210, providing a heat source for all the sample contact area(s). The beam expander 208 employs any known technology, including but not limited to the bean expanders described in U.S. Pat. Nos. 4,545,677, 4,214,813, 4,127,828, and 4,016,504, and U.S. Pat. Pub. No. 2008/0297912 and 2010/0214659, which are incorporated by reference in their entireties for all purposes.

Multiplexing

Figure 4:
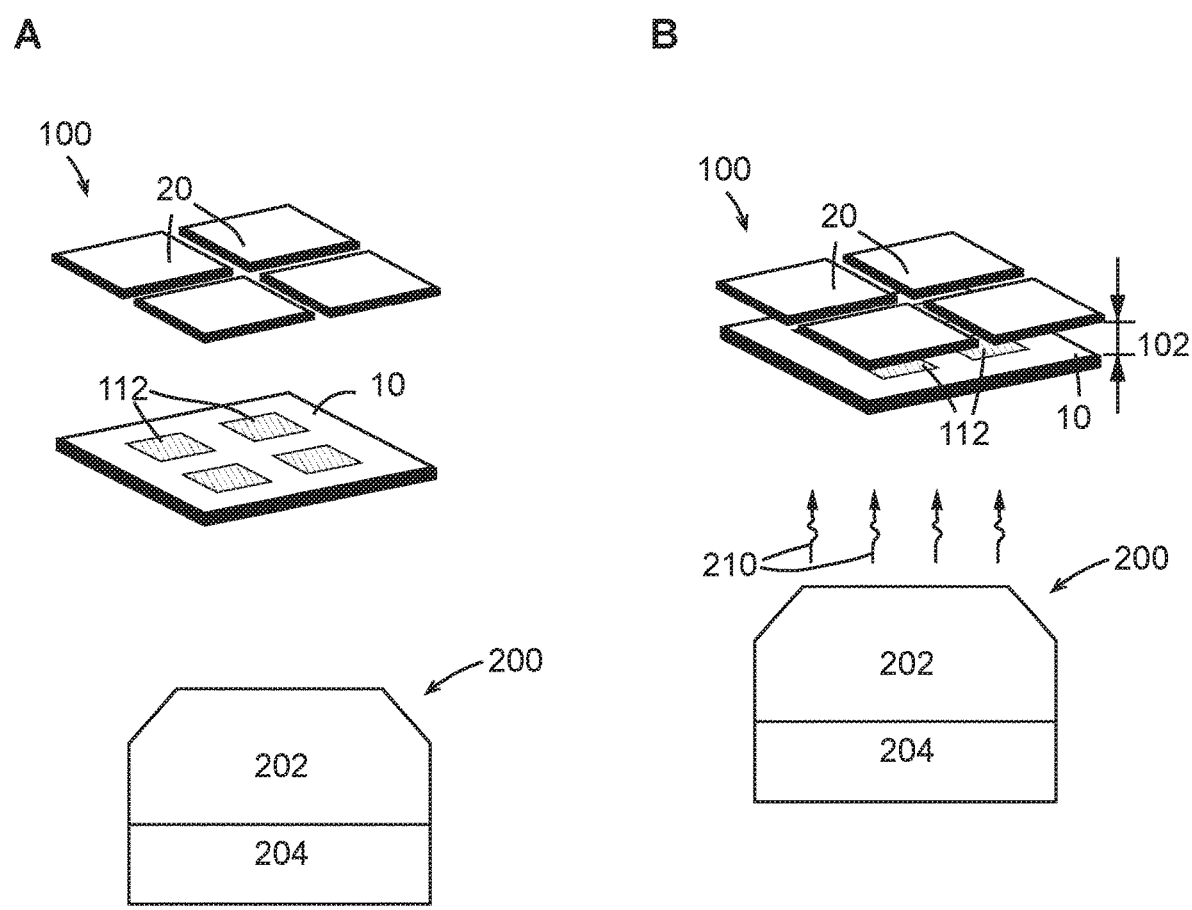
FIG. 4 shows perspective views of another embodiment of the present invention, where there are multiple sample contact areas on the plates, allowing the processing and analysis of multiple samples.

FIG. 4 shows perspective views of another embodiment of the present invention, where there are multiple sample contact areas on the plates, allowing the processing and analysis of multiple samples. As shown in panels (A) and (B) of FIG. 3, the thermal cycler system of the present invention comprises a sample unit 100 and a thermal control unit 200; the sample unit 100 comprises a first plate 10, a plurality of second plates 20, and a plurality of spacing mechanisms (not shown); the thermal control unit 200 comprises a radiation source 202 and a controller 204.

Referring to panel (A) of FIG. 4, one or both of the plates (e.g. the first plate 10) comprises a plurality of sample contact areas (not marked). In some embodiments, one or both of the plates (e.g. the first plate 10) comprises a plurality of radiation absorbing layers 112. Panel (A) of FIG. 4 shows the sample unit 100 in an open configuration, in which the first plate 10 and the second plates 20 are partially or entirely separated apart, allowing the deposition of one or more samples on one or both of the plates. In the open configuration, the spacing between the first plate 10 and the second plates 20 are not regulated by the spacing mechanisms.

Panel (B) of FIG. 4 shows the sample unit 100 in a closed configuration, in which the inner surfaces of the two plates face each other and the spacing 102 between the two plates are regulated by the spacing mechanism (not shown). If one or more samples have been deposited on the plates, the plates are configured to compress each sample into a layer, the thickness of the layer is regulated by the spacing mechanism.

As shown in panel (B) of FIG. 4, a plurality of second plates 20 is used to cover part of the first plate 10. For example, each second plate 20 covers a single sample contact area, onto which a sample is deposited. A spacing mechanism is present for each sample contact area and the spacing mechanisms have different heights, resulting in different spacing 102 for each sample contact area and for different thickness for each sample layer. For example, the spacing mechanism is pillar shaped spacers; each sample contact area has a set of spacers having a uniform height; different sets of spacers have the same or different heights, resulting in same or different sample layer thickness for the different samples.

Referring to panels (A) and (B) of FIG. 4, in some embodiments, the controller 204 directs the radiation source 202 to project a electromagnetic wave 210 to the first plate 10 (and thus the radiation absorbing layer 112), where the electromagnetic wave 210 is absorbed by the radiation absorbing layer 112 and converted to heat, resulting in change of temperature in the samples. In some embodiments, when there are multiple sample contact areas, multiple samples are processed and analyzed. For example, in certain embodiments each of the samples is a pre-mixed PCR reaction medium having different components. One sample unit 100 is used to test different conditions for amplifying the same nucleotide and/or amplifying different nucleotides with the same or different conditions.

EXEMPLARY EMBODIMENTS

Figure 5:
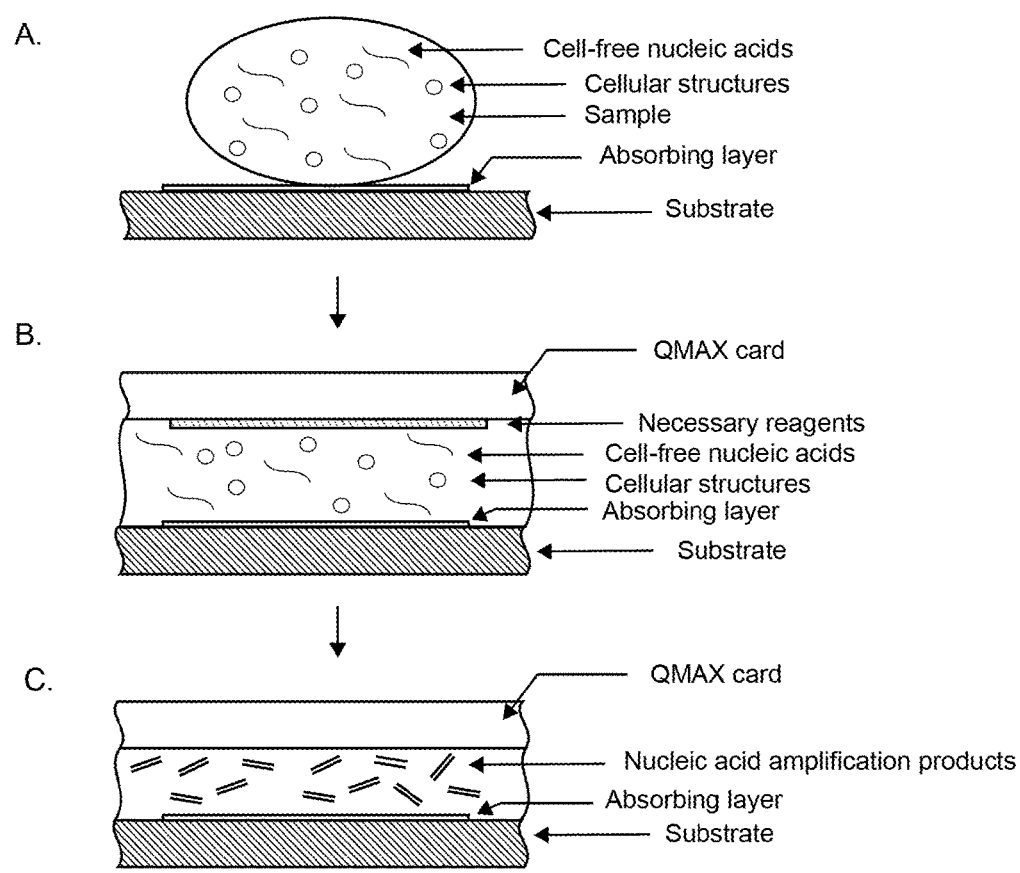
FIG. 5 shows a sectional view of an exemplary embodiment of the present invention, demonstrating how the sample is added and compressed.

FIG. 5 illustrates a cross-sectional view of an exemplary procedure for nucleic acid amplification using a QMAX card device. Examples of steps include (A) introducing sample containing nucleic acids onto the inner side of a first plate (substrate); (B) pressing a second plate (QMAX card) onto the inner surface of the first plate to form a closed configuration of the device, where necessary reagents for nucleic acid amplification are dried on the inner surface of the second plate; (c) accumulating nucleic acid amplification products in the chamber enclosed by the first and the second plates.

FIG. 5 illustrates a cross-sectional view of an exemplary procedure for nucleic acid amplification using a QMAX card device.

More particularly, in step (A), the "sample" can be any nucleic acid containing or not containing samples, including but not limited to human bodily fluids, such as whole blood, plasma, serum, urine, saliva, and sweat, and cell cultures (mammalian, plant, bacteria, fungi). The sample can be freshly obtained, or stored or treated in any desired or convenient way, for example by dilution or adding buffers, or other solutions or solvents. Cellular structures can exist in the sample, such as human cells, animal cells, plant cells, bacteria cells, fungus cells, and virus particles.

The term "nucleic acid" as used herein refers to any DNA or RNA molecule, or a DNA/RNA hybrid, or mixtures of DNA and/or RNA. The term "nucleic acid" therefore is intended to include but not limited to genomic or chromosomal DNA, plasmid DNA, amplified DNA, cDNA, total RNA, mRNA and small RNA. The term "nucleic acid" is also intended to include natural DNA and/or RNA molecule, or synthetic DNA and/or RNA molecule. In some embodiments, cell-free nucleic acids are presence in the sample, as used herein "cell-free" indicates nucleic acids are not contained in any cellular structures. In some other embodiments, nucleic acids are contained within cellular structures, which include but not limited to human cells, animal cells, plant cells, bacterial cells, fungi cells, and/or viral particles. Nucleic acids either in the form of cell-free nucleic acids or within cellular structures or a combination thereof, can be presence in the sample. In some further embodiments, nucleic acids are purified before introduced onto the inner surface of the first plate. In yet further embodiments, nucleic acids can be within a complex associated with other molecules, such as proteins and lipids.

The method of the invention is suitable for samples of a range of volumes. Sample having different volumes can be introduced onto the plates having different dimensions.

The sample can be introduced onto either the first plate or the second plate, or even both when necessary. FIG. 5. herein provides an example of introducing sample onto the first plate inner surface.

More particularly, in step (b), a second plate is pressed onto the inner surface of the first plate, in contact with the sample, to form a closed configuration of the device. As used herein, "a second plate" refers to a QMAX card with periodic spacers on the inner surface contacting samples.

As used herein, "nucleic acid amplification" includes any techniques used to detect nucleic acids by amplifying (generating numerous copies of) the target molecules in samples, herein "target" refers to a sequence, or partial sequence, of nucleic acid of interest. Suitable nucleic acid amplification techniques include but not limited to, different polymerase chain reaction (PCR) methods, such as hot-start PCR, nested PCR, touchdown PCR, reverse transcription PCR, RACE PCR, digital PCR, etc., and isothermal amplification methods, such as Loop-mediated isothermal amplification (LAMP), strand displacement amplification, helicase-dependent amplification, nicking enzyme amplification, rolling circle amplification, recombinase polymerase amplification, etc.

As used herein, "necessary reagents" include but not limited to, primers, deoxynucleotides (dNTPs), bivalent cations (e.g. Mg2+), monovalent cation (e.g. K+), buffer solutions, enzymes, and reporters. Necessary reagents for nucleic acid amplification can be either in the dry form on the inner surface of the first or the second plate or both, or in a liquid form encased in, embedded in, or surrounded by, a material that melts with increasing temperatures, such as, for example, paraffin.

As used herein, "primers", in some embodiments, can refer to a pair of forward and reverse primers. In some embodiments, primers can refer to a plurality of primers or primer sets. As used herein, enzymes suitable for nucleic acid amplification include, but not limited to, DNA-dependent polymerase, or RNA-dependent DNA polymerase, or DNA-dependent RNA polymerase.

As used herein, the term "reporter" refers to any tag, label, or dye that can bind to, or intercalate within, the nucleic acid molecule or be activated by byproducts of the amplification process to enable visualization of the nucleic acid molecule or the amplification process. Suitable reporters include but are not limited to fluorescent labels or tags or dyes, intercalating agents, molecular beacon labels, or bioluminescent molecules, or a combination thereof.

In some other embodiments, as used herein, "necessary reagents" can also include cell lysing reagent, which facilitates to break down cellular structures. Cell lysing reagents include but not limited to salts, detergents, enzymes, and other additives. The term "salts" herein include but not limited to lithium salt (e.g. lithium chloride), sodium salt (e.g. sodium chloride), potassium (e.g. potassium chloride). The term "detergents" herein can be ionic, including anionic and cationic, non-ionic or zwitterionic. The term "ionic detergent" as used herein includes any detergent, which is partly or wholly in ionic form when dissolved in water. Suitable anionic detergents include but not limited to sodium dodecyl sulphate (SDS) or other alkali metal alkylsulphate salts or similar detergents, sarkosyl, or combinations thereof. The term "enzymes" herein include but not limited to lysozyme, cellulase, and proteinase. In addition, chelating agents including but not limited to EDTA, EGTA and other polyamino carboxylic acids, and some reducing agents, such as dithiothreitol (dTT), can also be included in cell lysing reagents. The compositions of necessary reagents herein vary according to rational designs of different amplification reactions.

More particularly, in step (c), when the device is in the closed configuration, a radiation source projects an electromagnetic wave to the radiation absorbing layer on the inner or outer surface of the first plate, or the second plate or both. The radiation absorbing layer is configured to absorb the electromagnetic wave and convert at least a substantial portion of the energy from the said electromagnetic wave into the form of heat, which transmitted to the sample in the closed chamber. In some embodiments, the radiation source is programmed to adjust the temperature of the said sample in a range from ambient temperature to 98° C. In some embodiments, for example for conventional PCR, the sample is first heated to 98° C., and then undergoes a repeated cycle of 94° C., 50-65° C., and 72° C. for 15-40 times. In some embodiments, for example for isothermal amplification, the temperature of the sample is maintained at a constant temperature. In some embodiments, for example when conducting isothermal amplification via LAMP, the sample is heated to 60-65° C. for about 1-70 min.

As used herein, "nucleic acid amplification product" refers to various nucleic acids generated by nucleic acid amplification techniques. Types of nucleic acid amplification products herein include but not limited to single strand DNA, single strand RNA, double strand DNA, linear DNA, or circular DNA, etc. In some embodiments, nucleic acid amplification product can be identical nucleic acids having the same length and configuration. In some other embodiments, nucleic acid amplification products can be a plurality of nucleic acids having different lengths and configurations.

In some embodiments, nucleic acids accumulated after nucleic acid amplification is quantified using reporters. As defined and used above, reporter having quantifiable features that is correlated with the presence or the absence, or the amount of the nucleic acid amplicons accumulated in the closed chamber.

Figure 6:
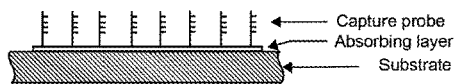
FIG. 6 shows a sectional view of an exemplary embodiment of the present invention, demonstrating a PCR process.
Figure 6:
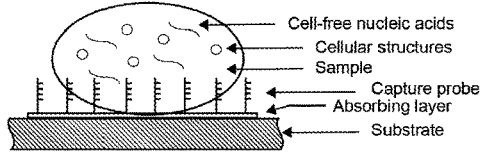
Figure 6:
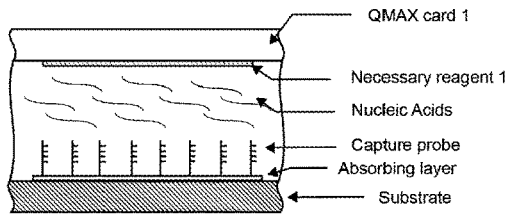
Figure 6:
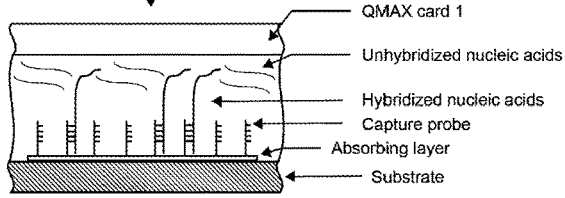
Figure 6:
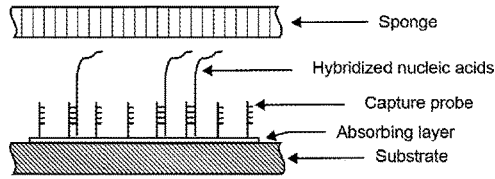
Figure 6:
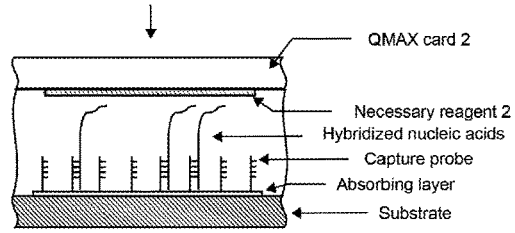
Figure 6:
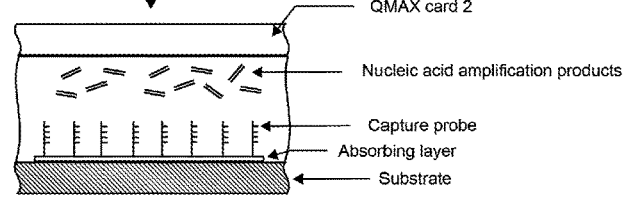

FIG. 6 illustrates a cross-sectional view of an exemplary assay procedure combining nucleic acid extraction and amplification using a QMAX card device. Examples of steps include (a) immobilizing capture probes on the inner surface of a first plate (substrate); (b) introducing samples onto the inner surface of the first plate; (c) pressing a second plate (QMAX card 1) onto the inner surface of the first plate to form a closed configuration of the device, where necessary reagents 1 to facilitate releasing and capturing nucleic acids are dried on the inner surface of the second plate; (d) capturing nucleic acids from the above said sample onto the inner surface of the first plate; (e) detaching the second plate and cleaning the inner surface of the first plate using sponge; (f) pressing a third plate (QMAX card 2) onto the inner surface of the first plate, where necessary reagents 2 for nucleic acid amplification are dried on the inner surface of the third plate; (g) accumulating nucleic acid amplification products in the chamber enclosed by the first and the third plate.

More particular, in step (a), capture probes are immobilized on the inner surface of the first plate. As used herein, "capture probes" refer to oligonucleotides having the length between 1-200 bp, preferably between 5-50 bp, more preferably between 10-20 bp. Capture probes have complementary sequence to nucleic acid sequences of interest in the sample. In some embodiments, identical capture probes are immobilized on the surface of the first plate. In some other embodiments, different capture probes having different base pair compositions are immobilized on the surface of the first plate. Capture probes can be DNA, or RNA, or both, but preferably to be single strand DNA. As used herein, "immobilize" refers to a process to anchor the capture probe on the plate surface. In some embodiments, capture probes are anchored through covalent bond, wherein, for example, either 5' or 3' end of the capture probe is modified to facilitate coating on the plate surface. Commonly used 3' end modifications include but not limited to thiol, dithiol, amine, biotin, etc. In some other embodiments, capture probes can be passively absorbed on the substrate surface.

After immobilized with capture probes, the plate surface is blocked with blocker solutions. Suitable blockers include but not limited to 6-Mercapto-hexanol, bovine serum albumin, etc.

As shown in step (b) in FIG. 6, the "sample" can be any nucleic acid containing or not containing samples, including but not limited to human bodily fluids, such as whole blood, plasma, serum, urine, saliva, and sweat, and cell cultures (mammalian, plant, bacteria, fungi). The sample can be freshly obtained, or stored or treated in any desired or convenient way, for example by dilution or adding buffers, or other solutions or solvents. Cellular structures can exist in the sample, such as human cells, animal cells, plant cells, bacteria cells, fungus cells, and virus particles.

The term "nucleic acid" as used herein refers to any DNA or RNA molecule, or a DNA/RNA hybrid, or mixtures of DNA and/or RNA. The term "nucleic acid" therefore is intended to include but not limited to genomic or chromosomal DNA, plasmid DNA, amplified DNA, cDNA, total RNA, mRNA and small RNA. The term "nucleic acid" is also intended to include natural DNA and/or RNA molecule, or synthetic DNA and/or RNA molecule. In some embodiments, cell-free nucleic acids are presence in the sample, as used herein "cell-free" indicates nucleic acids are not contained in any cellular structures. In some other embodiments, nucleic acids are contained within cellular structures, which include but not limited to human cells, animal cells, plant cells, bacterial cells, fungi cells, and/or viral particles. Nucleic acids either in the form of cell-free nucleic acids or within cellular structures or a combination thereof, can be presence in the sample. In some further embodiments, nucleic acids are purified before introduced onto the inner surface of the first plate. In yet further embodiments, nucleic acids can be within a complex associated with other molecules, such as proteins and lipids.

The method of the invention is suitable for samples of a range of volumes. Sample having different volumes can be introduced onto the plates having different dimensions.

The sample can be introduced onto either the first plate or the second plate, or even both when necessary. FIG. 6 herein provides an example of introducing sample onto the first plate inner surface.

More particularly, in step (c), a second plate (QMAX card 1) is pressed onto the inner surface of the first plate (substrate), in contact with the sample, to form a closed configuration of the device. Necessary reagents 1 for nucleic acid amplification can be either in the dry form on the inner surface of the first or the second plate or both, or in a liquid form encased in, embedded in, or surrounded by, a material that melts with increasing temperatures, such as, for example, paraffin.

As used herein, "necessary reagent 1" refer to cell lysing reagent, or hybridization reagents, or a combination thereof.

As used herein, "cell lysing reagents", intend to include but not limited to salts, detergents, enzymes, and other additives, which facilitates to disrupt cellular structures. The term "salts" herein include but not limited to lithium salt (e.g. lithium chloride), sodium salt (e.g. sodium chloride), potassium (e.g. potassium chloride). The term "detergents" herein can be ionic, including anionic and cationic, non-ionic or zwitterionic. The term "ionic detergent" as used herein includes any detergent which is partly or wholly in ionic form when dissolved in water. Suitable anionic detergents include but not limited to sodium dodecyl sulphate (SDS) or other alkali metal alkyl sulphate salts or similar detergents, sarkosyl, or combinations thereof. The term "enzymes" herein include but not limited to lysozyme, cellulase, and proteinase. In addition, chelating agents including but not limited to EDTA, EGTA and other polyamino carboxylic acids, and some reducing agents, such as dithiotreitol (dTT), can also be included in cell lysing reagents. The compositions of necessary reagents herein vary according to rational designs of different amplification reactions.

As used herein, "hybridization reagents" refer to reagents that facilitate the hybridization between immobilized capture probes and nucleic acid of interest in the sample, herein including but not limited to sodium chloride, sodium acetate, ficoll, dextran, polyvinylpyrrolidone, bovine serum albumin, etc.

More particularly, in step (d), after in contact with the above said sample, dried necessary reagent 1 dissolves in the sample. Nucleic acids of interest, either released from disrupted cellular structures or presence as cell-free nucleic acids, or a combination thereof, hybridize to the complementary capture probes on the plate surface. Time used for hybridization varies, largely depending on the specifications of the spacers on the inner surface of the QMAX card 1. In some embodiments, for example, when a QMAX card 1 having 30 um spacers in height is used, experimental data indicated after 2 min, hybridization between nucleic acids of interest and immobilized capture probes reached equilibrium. As used herein FIG. 6 (d), "unhybridized nucleic acids" refer to nucleic acids that are not captured by the immobilized capture probes.

More particularly, in step (e), the second plate (QMAX card 1) is detached from the first plate (substrate) and the surface of the first plate (substrate) is cleaned using sponge. As used herein, "sponge" refers to a class of flexible porous materials that change pore sizes under different pressures. Sponges containing washing buffer are in contact with the first plate surface to remove contaminates. In some embodiments, sponges are in contact with the first plate surface for one time. In some other embodiments, sponges are in contact with the first plate surface for twice, or more than twice. As used herein, "contaminates" refer to compounds including but not limited to cell debris, proteins, non-specific nucleic acid, etc. that are detrimental to the nucleic acid amplification reaction.

More particularly, in step (f), a third plate (QMAX card 2) is pressed onto the inner surface of the first plate, in contact with the sample, to form a closed configuration of the device. Necessary reagent 2 for nucleic acid amplification can be either in the dry form on the inner surface of the first or the third plate or both, or in a liquid form encased in, embedded in, or surrounded by, a material that melts with increasing temperatures, such as, for example, paraffin.

As used herein, "nucleic acid amplification" includes any techniques used to detect nucleic acids by amplifying (generating numerous copies of) the target molecules in samples, herein "target" refers to a sequence, or partial sequence, of nucleic acid of interest. Suitable nucleic acid amplification techniques include but not limited to, different polymerase chain reaction (PCR) methods, such as hot-start PCR, nested PCR, touchdown PCR, reverse transcription PCR, RACE PCR, digital PCR, etc., and isothermal amplification methods, such as Loop-mediated isothermal amplification, strand displacement amplification, helicase-dependent amplification, nicking enzyme amplification, rolling circle amplification, recombinase polymerase amplification, etc.

As used herein, "necessary reagent 2" include but not limited to, primers, deoxynucleotides (dNTPs), bivalent cations (e.g. Mg2+), monovalent cation (e.g. K+), buffer solutions, enzymes, and reporters. Necessary reagent 2 for nucleic acid amplification can be either in the dry form on the inner surface of the first or the second plate or both, or in a liquid form encased in, embedded in, or surrounded by, a material that melts with increasing temperatures, such as, for example, paraffin.

As used herein, "primers", in some embodiments, can refer to a pair of forward and reverse primers. In some embodiments, primers can refer to a plurality of primers or primer sets. As used herein, enzymes suitable for nucleic acid amplification include, but not limited to, DNA-dependent polymerase, or RNA-dependent DNA polymerase, or DNA-dependent RNA polymerase.

As used herein, the term "reporter" refers to any tag, label, or dye that can bind to, or intercalate within, the nucleic acid molecule or be activated by byproducts of the amplification process to enable visualization of the nucleic acid molecule or the amplification process. Suitable reporters include but are not limited to fluorescent labels or tags or dyes, intercalating agents, molecular beacon labels, or bioluminescent molecules, or a combination thereof.

More particularly, in step (g), when the device is in the closed configuration, a radiation source projects an electromagnetic wave to the radiation absorbing layer on the inner or outer surface of the first plate, or the third plate or both. The radiation absorbing layer is configured to absorb the electromagnetic wave and convert at least a substantial portion of the energy from the said electromagnetic wave into the form of heat, which transmitted to the sample in the closed chamber. In some embodiments, the radiation source is programmed to adjust the temperature of the said sample in a range from ambient temperature to 98° C. In some embodiments, for example for conventional PCR, the sample is first heated to 98° C., and then undergoes a repeated cycle of 94° C., 50-65° C., and 72° C. for 15-40 times. In some embodiments, for example for isothermal amplification, the temperature of the sample is maintained at a constant temperature. In some embodiments, for example when conducting isothermal amplification via LAMP, the sample is heated to 60-65° C. for about 1-70 min.

As used herein, "nucleic acid amplification product" refers to various nucleic acids generated by nucleic acid amplification techniques. Types of nucleic acid amplification products herein include but not limited to single strand DNA, single strand RNA, double strand DNA, linear DNA, or circular DNA, etc. In some embodiments, nucleic acid amplification product can be identical nucleic acids having the same length and configuration. In some other embodiments, nucleic acid amplification products can be a plurality of nucleic acids having different lengths and configurations.

In some embodiments, nucleic acids accumulated after nucleic acid amplification is quantified using reporters. As defined and used above, reporter having quantifiable features that is correlated with the presence or the absence, or the amount of the nucleic acid amplicons accumulated in the closed chamber.

In some embodiments of QMAX, the sample contact area of one or both of the plates comprises a compressed open flow monitoring surface structures (MSS) that are configured to monitoring how much flow has occurred after COF. For examples, the MSS comprises, in some embodiments, shallow square array, which will cause friction to the components (e.g. blood cells in a blood) in a sample. By checking the distributions of some components of a sample, one can obtain information related to a flow, under a COF, of the sample and its components.

The depth of the MSS can be $1/1000$, $1/100$, $1/100$, $1/5$, $1/2$ of the spacer height or in a range of any two values, and in either protrusion or well form.

In some embodiments, a device for assaying a thin fluidic sample layer, comprising:
  a first plate, a second plate, spacers, and a clamp, wherein:
    i. the first plate and the second plate are movable relative to each other into different configurations, including an open configuration and a closed configuration;
    ii. each of the plates comprises, on its respective surface, a sample contact area for contacting a fluidic sample;
    iii. one or both of the plates comprise the spacers that are fixed to the respective plate;
    iv. the spacers have a predetermined substantially uniform height that is equal to or less than 200 microns, wherein at least one of the spacers is inside the sample contact area; and
    v. the clamp that compresses the first plate and the second plate to fix the two plates together at the closed configuration, wherein the pressure of the clamp inserted on the plates is 0.01 kg/cm^2 or higher,
    wherein in an open configuration, the two plates are partially or completely separated apart, the spacing between the plates is not regulated by the spacers, and the sample is deposited on one or both of the plates; and
    wherein in a closed configuration, which is configured after the sample is deposited in the open configuration, at least a part of the sample is compressed by the two plates into a layer of substantially uniform thickness and is substantially stagnant relative to the plates, wherein the uniform thickness of the layer is confined by the sample contact areas of the two plates and is regulated by the plates and the spacers.

In some embodiments, A device for rapidly changing temperature of a thin fluidic sample layer, comprising:
  a first plate, a second plate, spacers, and a clamp, wherein:
    vi. the first plate and the second plate are movable relative to each other into different configurations, including an open configuration and a closed configuration;

vii. each of the plates comprises, on its respective surface, a sample contact area for contacting a fluidic sample;

viii. one or both of the plates comprise the spacers that are fixed to the respective plate;

ix. the spacers have a predetermined substantially uniform height that is equal to or less than 200 microns, wherein at least one of the spacers is inside the sample contact area; and x. the clamp that compresses the first plate and the second plate to fix the two plates together at the closed configuration, wherein the pressure of the clamp inserted on the plates is 0.01 kg/cm^2 or higher, wherein in an open configuration, the two plates are partially or completely separated apart, the spacing between the plates is not regulated by the spacers, and the sample is deposited on one or both of the plates; and wherein in a closed configuration, which is configured after the sample is deposited in the open configuration, at least a part of the sample is compressed by the two plates into a layer of substantially uniform thickness and is substantially stagnant relative to the plates, wherein the uniform thickness of the layer is confined by the sample contact areas of the two plates and is regulated by the plates and the spacers; and wherein the plates and the clamp are configured to allow a temperature of the sample changed at a rate of 10° C./s or higher.

In some embodiments, a device for rapidly changing temperature of a thin fluidic sample layer, comprising: a first plate, a second plate, and spacers, wherein:

iii. the first plate has a thickness of 100 um (micron) or less;

iv. the first plate and the second plate are movable relative to each other into different configurations, including an open configuration and a closed configuration;

v. each of the plates comprises, on its respective surface, a sample contact area for contacting a fluidic sample;

vi. one or both of the plates comprise the spacers that are fixed to the respective plate;

vii. the spacers have a predetermined substantially uniform height that is equal to or less than 200 microns;

viii. at least one of the spacers is inside the sample contact area;

wherein in an open configuration, the two plates are partially or completely separated apart, the spacing between the plates is not regulated by the spacers, and the sample is deposited on one or both of the plates; and wherein in a closed configuration, which is configured after the sample is deposited in the open configuration, at least a part of the sample is compressed by the two plates into a layer of substantially uniform thickness and is substantially stagnant relative to the plates, wherein the uniform thickness of the layer is confined by the sample contact areas of the two plates and is regulated by the plates and the spacers; and wherein the plates and the clamp are configured to allow a temperature of at least a part of the sample to be changed at a rate of 10° C./s or higher.

In some embodiments, a device for rapidly changing temperature of a thin fluidic sample layer, comprising:

a first plate, a second plate, and a clamp, wherein:

i. the first plate and the second plate are movable relative to each other into different configurations, including an open configuration and a closed configuration;

ii. each of the plates comprises, on its respective surface, a sample contact area for contacting a fluidic sample to be assayed; and iii. the clamp that compresses the first plate and the second plate to fix the plates at the closed configuration, wherein the pressure of the clamp inserted on the plates is 0.01 kg/cm^2 or higher, wherein in an open configuration, the two plates are partially or completely separated apart, the average spacing between the plates is 250 um or larger, and the sample is deposited on one or both of the plates; and wherein in a closed configuration, which is configured after the sample is deposited in the open configuration, at least a part of the sample is compressed by the two plates into a layer of substantially uniform thickness and is substantially stagnant relative to the plates, wherein the uniform thickness of the layer is confined by the sample contact areas of the two plates and is 200 um thick or less.

In some embodiments, the device of any prior embodiments, further comprising a radiation absorbing lay near the at least part of the sample of uniform thickness, whereas the area of the at least part of the sample and the radiation absorbing layer are substantially larger than the uniform thickness.

In some embodiments, the device of any prior embodiments, wherein the area of the at least part of the sample and the radiation absorbing layer are substantially larger than the uniform thickness of the sample.

In some embodiments, wherein the device has one of the plates of a thickness of 100 um or less.

In some embodiments, further comprising a radiation absorbing lay near the at least part of the sample of uniform thickness, wherein the device has one of the plates of a thickness of 100 um or less.

In some embodiments, further comprising a clamp that compresses the first plate and the second plate together in the closed configuration, wherein the pressure of the clamp inserted on the plates is 0.01 kg/cm^2 or higher.

In some embodiments, further comprising a clamp that compresses the first plate and the second plate together in the closed configuration, and further comprising a radiation absorbing lay near the at least part of the sample of uniform thickness, wherein the pressure of the clamp inserted on the plates is 0.01 kg/cm^2 or higher.

In some embodiments, a system for rapidly changing temperature of a thin fluidic sample layer, comprising:

i. a device of any prior embodiments, ii. a radiation source, wherein the radiation source is configured to radiate electromagnetic waves that the radiation absorbing layer absorbs significantly; and iii. a controller is configured to control the radiation source and change the temperature of the sample.

In some embodiments, a method for rapidly changing temperature of a thin fluidic sample layer, comprising:

i. providing a device or a system of any prior embodiments;

ii. depositing a fluid sample on one or both of the plates of the device;

iii. after ii, pressing the plates into a closed configuration wherein the plates compress at least a part of the sample into a thin layer of a thickness less than 200 um; and iv. changing and maintaining the temperature of the sample layer by changing the presence, intensity, wavelength, frequency, and/or angle of the electromagnetic waves from the radiation source.

In some embodiments, the device, system, or method of any prior embodiments, wherein the clamp is configured to comprise a heat insulator layer to reduce the heat conduction between the clamp and the plates, wherein the heat insulator layer comprises a material of a thermal conductivity of 2 W/m-K.

In some embodiment, the device, system, or method of any prior embodiments, wherein the clamp is configured to comprise a heat insulator layer to reduce thermal mass that needs to heating or cooling the sample, wherein the heat insulator layer comprises a material of a thermal conductivity of 2 W/m-K.

In some embodiment, the device, system, or method of any prior embodiments, wherein, in a close configuration, the clamp is configured to seal all the QMAX card.

In some embodiment, the device, system, or method of any prior embodiments, wherein, in a close configuration, the clamp is configured to have thermal conduction contact with a part of the surface of the plates.

In some embodiment, the device, system, or method of any prior embodiments, wherein, in a close configuration, the clamp has a thermal conduction contact with only the peripheral surface area of the plates.

In some embodiment, the device, system, or method of any prior embodiments, wherein, in a close configuration, the clamp has a thermal conduction contact with only a surface area of the plates, wherein the surface area is outside the portion of the sample that nucleic acids to be amplified.

In some embodiment, the device, system, or method of any prior embodiments, wherein the clamp comprises a window that is transparent allowing light outside going to the plates or the light inside plates going out.

In some embodiment, the device, system, or method of any prior embodiments, wherein the clamp comprises a window that is transparent allowing light outside going to the plates or the light inside plates going out, wherein the transparence is above 30%, 40%, 50%, 60%, 70%, 80%, 90%, 100%, or a range between any two of the values.

In some embodiment, the device, system, or method of any prior embodiments, wherein the clamp insert a pressure to compress the first plates and the second plates, wherein the pressure is 0.01 kg/cm2, 0.1 kg/cm2, 0.5 kg/cm2, 1 kg/cm2, 2 kg/cm2, kg/cm2, 5 kg/cm2, 10 kg/cm2, 20 kg/cm2, 30 kg/cm2, 40 kg/cm2, 50 kg/cm2, 60 kg/cm2, 100 kg/cm2, 150 kg/cm2, 200 kg/cm2, 400 kg/cm2, or a range between any two of the values.

In some embodiment, the device, system, or method of any prior embodiments, wherein the clamp insert a pressure to compress the first plates and the second plates, wherein the pressure is from 0.1 kg/cm2 to 20 kg/cm2.

In some embodiment, the device, system, or method of any prior embodiments, wherein the clamp insert a pressure to compress the first plates and the second plates, wherein the pressure is from 0.1 kg/cm2 to 20 kg/cm2.

In some embodiment, the device, system, or method of any prior embodiments, wherein the clamp insert a pressure to compress the first plates and the second plates, wherein the pressure is from 0.5 kg/cm2 to 40 kg/cm2.

In some embodiment, the device, system, or method of any prior embodiments, further comprising a clamp that compresses the first plate and the second plate together in the closed configuration, and further comprising a sealing material between at least part of the first plate and the second plate, wherein the pressure of the clamp inserted on the plates is 0.01 kg/cm^2 or higher.

In some embodiment, the device, system, or method of any prior embodiments, wherein the spacer has subtainilaly flat top.

In some embodiment, the device, system, or method of any prior embodiments, wherein one of the plate is 50 um or less. In some embodiments, the device, system, or method of any prior embodiments, wherein the changing temperature of the sample is a thermal cycling that changes the temperature up and down in cyclic fashion.

In some embodiments, the device, system, or method of any prior embodiments, wherein the changing temperature of the sample is a thermal cycling, wherein the thermal cycling is for amplification of nucleic acid using polymerase chain action (PCR).

In some embodiments, the device, system, or method of any prior embodiments, wherein the changing of the temperature of the sample is for isothermal amplification of nucleic acid.

In some embodiments, the device, system, or method of any prior embodiments, the area of the at least part of the sample and the radiation absorbing layer are substantially larger than the uniform thickness.

In some embodiments, the device, system, or method of any prior embodiments, wherein the radiation absorbing layer comprises a disk-coupled dots-on-pillar antenna (D2PA) array, silicon sandwich, graphene, superlattice or other plasmonic materials, other a combination thereof.

In some embodiments, the device, system, or method of any prior embodiments, wherein the radiation absorbing layer comprises carbon or black nanostructures or a combination thereof.

In some embodiments, he device, system, or method of any prior embodiments, wherein the radiation absorbing layer is configured to absorb radiation energy.

In some embodiments, the device, system, or method of any prior embodiments, wherein the radiation absorbing layer is configured to radiate energy in the form of heat after absorbing radiation energy.

In some embodiments, the device, system, or method of any prior embodiments, wherein the radiation absorbing layer is positioned underneath the sample layer and in direct contact with the sample layer.

In some embodiments, the device, system, or method of any prior embodiments, wherein the radiation absorbing layer is configured to absorbing electromagnetic waves selected from the group consisting of: radio waves, microwaves, infrared waves, visible light, ultraviolet waves, X-rays, gamma rays, and thermal radiation.

In some embodiments, the device, system, or method of any prior embodiments, wherein at least one of the plates does not block the radiation that the radiation absorbing layer absorbs.

In some embodiments, the device, system, or method of any prior embodiments, wherein one or both of the plates have low thermal conductivity.

In some embodiments, the device, system, or method of any prior embodiments, wherein the uniform thickness of the sample layer is regulated by one or more spacers that are fixed to one or both of the plates.

In some embodiments, the device, system, or method of any prior embodiments, wherein the sample is a pre-mixed polymerase chain reaction (PCR) medium.

In some embodiments, the device, system, or method of any prior embodiments, 1, wherein the device is configured to facilitate PCR assays for changing temperature of the sample according to a predetermined program.

In some embodiments, the device, system, or method of any prior embodiments, wherein the device is configured to conduct diagnostic testing, health monitoring, environmental testing, and/or forensic testing.

In some embodiments, the device, system, or method of any prior embodiments, wherein the device is configured to conduct DNA amplification, DNA quantification, selective DNA isolation, genetic analysis, tissue typing, oncogene identification, infectious disease testing, genetic fingerprinting, and/or paternity testing.

In some embodiments, the device of any prior embodiments, wherein the sample layer is laterally sealed to reduce sample evaporation.

In some embodiments, the system of any of embodiments, further comprising a controller, which is configured to control the presence, intensity, wavelength, frequency, and/or angle of the electromagnetic waves.

In some embodiments, the system of any prior embodiments, further comprising a thermometer, which is configured to measure the temperature at or in proximity of the sample contact area and send a signal to the controller based on the measured temperature.

In some embodiments, the system or method of any prior embodiments, wherein the thermometer is selected from the group consisting of: fiber optical thermometer, infrared thermometer, liquid crystal thermometer, pyrometer, quartz thermometer, silicon bandgap temperature sensor, temperature strip, thermistor, and thermocouple.

In some embodiments, the system or method of any prior embodiments, wherein the controller is configured to control the present, intensity, wavelength, frequency, and/or angle of the electromagnetic waves from the radiation source.

In some embodiments, the system or method of any prior embodiments, wherein the radiation source and the radiation absorbing layer are configured that the electromagnetic waves cause an average ascending temperature rate ramp of at least 10° C./s; and the removal of the electromagnetic waves results in an average descending temperature rate ramp of at least 5° C./s.

In some embodiments, the device, system, or method of any prior embodiments, wherein the radiation source and the radiation absorbing layer are configured to create an average ascending temperature rate ramp of at least 10° C./s and an average descending temperature rate ramp of at least 5° C./s.

In some embodiments, the device, system, or method of any prior embodiments, wherein the radiation source and the radiation absorbing layer are configured to create an average ascending temperature rate ramp of at least 10° C./s to reach the initialization step, the denaturation step and/or the extension/elongation step during a PCR, and an average descending temperature rate ramp of at least 5° C./s to reach the annealing step and/or the final cooling step during a PCR.

In some embodiments, the device, system, or method of any prior embodiments, wherein the PCR sample comprises: template DNA, primer DNA, cations, polymerase, and buffer.

In some embodiments, the method of any prior embodiments, wherein the step of pressing the plates into a closed figuration comprises pressing the plates with an imprecise pressing force.

In some embodiments, the method of any prior embodiments, wherein the step of pressing the plates into a closed figuration comprises pressing the plates directly with human hands.

In some embodiments, the method of any prior embodiments, wherein the layer of highly uniform thickness has a thickness variation of less than 10%.

In some embodiments, the device, system, or method of any prior embodiments, further comprising reagents selected from DNA template, primers, DNA polymerase, deoxynucleoside triphosphates (dNTPs), bivalent cations (e.g. $Mg^{2+}$), monovalent cation (e.g. $K^+$), and buffer solution.

In some embodiments, the device, system, or method of any prior claims, wherein the changing temperature of the sample is a thermal cycling, wherein the thermal cycling is for amplification of nucleic acid using polymerase chain action (PCR), that is selected from a group of hot-start PCR, nested PCR, touchdown PCR, reverse transcription PCR, RACE PCR, and digital PCR.

In some embodiments, the device, system, or method of any prior claims, wherein the changing of the temperature of the sample is for isothermal amplification of nucleic acid, that is selected from a group of Loop-mediated isothermal amplification, strand displacement amplification, helicase-dependent amplification, nicking enzyme amplification, rolling circle amplification, and recombinase polymerase amplification.

Flat Top of Pillar Spacers

In certain embodiments of the present invention, the spacers are pillars that have a flat top and a foot fixed on one plate, wherein the flat top has a smoothness with a small surface variation, and the variation is less than 5, 10 nm, 20 nm, 30 nm, 50 nm, 100 nm, 200 nm, 300 nm, 400 nm, 500 nm, 600 nm, 700 nm, 800 nm, 1000 nm, or in a range between any two of the values. A preferred flat pillar top smoothness is that surface variation of 50 nm or less.

Furthermore, the surface variation is relative to the spacer height and the ratio of the pillar flat top surface variation to the spacer height is less than 0.5%, 1%, 3%, 5%, 7%, 10%, 15%, 20%, 30%, 40%, or in a range between any two of the values. A preferred flat pillar top smoothness has a ratio of the pillar flat top surface variation to the spacer height is less than 2%, 5%, or 10%.

Sidewall Angle of Pillar Spacers

In certain embodiments of the present invention, the spacers are pillars that have a sidewall angle. In some embodiments, the sidewall angle is less than 5 degree (measured from the normal of a surface), 10 degree, 20 degree, 30 degree, 40 degree, 50 degree, 70 degree, or in a range between any two of the values. In a preferred embodiment, the sidewall angle is less 5 degree, 10 degree, or 20 degree.

Formation of Uniform Thin Fluidic Layer by an Imprecise Force Pressing

In certain embodiment of the present invention, a uniform thin fluidic sample layer is formed by using a pressing with an imprecise force. The term "imprecise pressing force" without adding the details and then adding a definition for imprecise pressing force. As used herein, the term "imprecise" in the context of a force (e.g. "imprecise pressing force") refers to a force that (a) has a magnitude that is not precisely known or precisely predictable at the time the force is applied; (b) has a pressure in the range of 0.01 kg/cm² (centimeter square) to 100 kg/cm², (c) varies in magnitude from one application of the force to the next; and (d) the imprecision (i.e. the variation) of the force in (a) and (c) is at least 20% of the total force that actually is applied.

An imprecise force can be applied by human hand, for example, e.g., by pinching an object together between a thumb and index finger, or by pinching and rubbing an object together between a thumb and index finger.

In some embodiments, the imprecise force by the hand pressing has a pressure of 0.01 kg/cm2, 0.1 kg/cm2, 0.5 kg/cm2, 1 kg/cm2, 2 kg/cm2, kg/cm2, 5 kg/cm2, 10 kg/cm2, 20 kg/cm2, 30 kg/cm2, 40 kg/cm2, 50 kg/cm2, 60 kg/cm2, 100 kg/cm2, 150 kg/cm2, 200 kg/cm2, or a range between any two of the values; and a preferred range of 0.1 kg/cm2 to 0.5 kg/cm2, 0.5 kg/cm2 to 1 kg/cm2, 1 kg/cm2 to 5 kg/cm2, 5 kg/cm2 to 10 kg/cm2 (Pressure).

Spacer Filling Factor.

The term "spacer filling factor" or "filling factor" refers to the ratio of the spacer contact area to the total plate area", wherein the spacer contact area refers, at a closed configuration, the contact area that the spacer's top surface contacts to the inner surface of a plate, and the total plate area refers the total area of the inner surface of the plate that the flat top of the spacers contact. Since there are two plates and each spacer has two contact surfaces each contacting one plate, the filling fact is the filling factor of the smallest.

For example, if the spacers are pillars with a flat top of a square shape (10 um×10 um), a nearly uniform cross-section and 2 um tall, and the spacers are periodic with a period of 100 um, then the filing factor of the spacer is 1%. If in the above example, the foot of the pillar spacer is a square shape of 15 um×15 um, then the filling factor is still 1% by the definition.

The method or device of any prior claim, wherein the spacers have pillar shape and nearly uniform cross-section.

The method or device of any prior claim, wherein the inter spacer distance (SD) is equal or less than about 120 um (micrometer).

The method or device of any prior claim, wherein the inter spacer distance (SD) is equal or less than about 100 um (micrometer).

The method or device of any prior claim, wherein the fourth power of the inter-spacer-distance (ISD) divided by the thickness (h) and the Young's modulus (E) of the flexible plate ($ISD^4/(hE)$) is $5 \times 10^6$ um$^3$/GPa or less.

The method or device of any prior claim, wherein the fourth power of the inter-spacer-distance (ISD) divided by the thickness (h) and the Young's modulus (E) of the flexible plate ($ISD^4/(hE)$) is $5 \times 10^5$ um$^3$/GPa or less.

The method or device of any prior claim, wherein the spacers have pillar shape, a substantially flat top surface, a predetermined substantially uniform height, and a predetermined constant inter-spacer distance that is at least about 2 times larger than the size of the analyte, wherein the Young's modulus of the spacers times the filling factor of the spacers is equal or larger than 2 MPa, wherein the filling factor is the ratio of the spacer contact area to the total plate area, and wherein, for each spacer, the ratio of the lateral dimension of the spacer to its height is at least 1 (one).

The method or device of any prior claim, wherein the spacers have pillar shape, a substantially flat top surface, a predetermined substantially uniform height, and a predetermined constant inter-spacer distance that is at least about 2 times larger than the size of the analyte, wherein the Young's modulus of the spacers times the filling factor of the spacers is equal or larger than 2 MPa, wherein the filling factor is the ratio of the spacer contact area to the total plate area, and wherein, for each spacer, the ratio of the lateral dimension of the spacer to its height is at least 1 (one), wherein the fourth power of the inter-spacer-distance (ISD) divided by the thickness (h) and the Young's modulus (E) of the flexible plate ($ISD^4/(hE)$) is $5 \times 10^6$ um$^3$/GPa or less.

The device of any prior device claim, wherein the ratio of the inter-spacing distance of the spacers to the average width of the spacer is 2 or larger, and the filling factor of the spacers multiplied by the Young's modulus of the spacers is 2 MPa or larger.

The device or method of any prior claim, wherein the analyte is protein, peptide, nucleic acids, virus, bacterial, cell, nanoparticle, molecule, synthetic compounds, or inorganic compounds.

The method or device of any prior claim, wherein the sample is a biological sample selected from amniotic fluid, aqueous humour, vitreous humour, blood (e.g., whole blood, fractionated blood, plasma or serum), breast milk, cerebrospinal fluid (CSF), cerumen (earwax), chyle, chime, endolymph, perilymph, feces, breath, gastric acid, gastric juice, lymph, mucus (including nasal drainage and phlegm), pericardial fluid, peritoneal fluid, pleural fluid, pus, rheum, saliva, exhaled breath condensates, sebum, semen, sputum, sweat, synovial fluid, tears, vomit, and urine.

The method or device of any prior claim, wherein the spacers have a shape of pillars and a ratio of the width to the height of the pillar is equal or larger than one.

The method of any prior claim, wherein the sample that is deposited on one or both of the plates has an unknown volume.

The method or device of any prior claim, wherein the spacers have a shape of pillar, and the pillar has substantially uniform cross-section.

The method or device of any prior claim, wherein the samples is for the detection, purification and quantification of chemical compounds or biomolecules that correlates with the stage of certain diseases.

The method or device of any prior claim, wherein the samples is related to infectious and parasitic disease, injuries, cardiovascular disease, cancer, mental disorders, neuropsychiatric disorders, pulmonary diseases, renal diseases, and other and organic diseases.

The method or device of any prior claim, wherein the samples is related to the detection, purification and quantification of microorganism.

The method or device of any prior claim, wherein the samples is related to virus, fungus and bacteria from environment, e.g., water, soil, or biological samples.

The method or device of any prior claim, wherein the samples is related to the detection, quantification of chemical compounds or biological samples that pose hazard to food safety or national security, e.g. toxic waste, anthrax.

The method or device of any prior claim, wherein the samples is related to quantification of vital parameters in medical or physiological monitor.

The method or device of any prior claim, wherein the samples is related to glucose, blood, oxygen level, total blood count.

The method or device of any prior claim, wherein the samples is related to the detection and quantification of specific DNA or RNA from biosamples.

The method or device of any prior claim, wherein the samples is related to the sequencing and comparing of genetic sequences in DNA in the chromosomes and mitochondria for genome analysis.

The method or device of any prior claim, wherein the samples is related to detect reaction products, e.g., during synthesis or purification of pharmaceuticals.

The method or device of any prior claim, wherein the samples is cells, tissues, bodily fluids, and stool.

The method or device of any prior claim, wherein the sample is the sample in the fields of human, veterinary, agriculture, foods, environments, and drug testing.

The method or device of any prior claim, wherein the sample is a biological sample is selected from hair, finger nail, ear wax, breath, connective tissue, muscle tissue, nervous tissue, epithelial tissue, cartilage, cancerous sample, or bone.

The devices or methods of any prior embodiment, wherein the inter-spacer distance is in the range of 5 $\mu$m to 120 $\mu$m.

The devices or methods of any prior embodiment, wherein the inter-spacer distance is in the range of 120 $\mu$m to 200 $\mu$m.

The device of any prior device claim, wherein the flexible plates have a thickness in the range of 20 um to 250 um and Young's modulus in the range 0.1 to 5 GPa.

The device of any prior device claim, wherein for a flexible plate, the thickness of the flexible plate times the Young's modulus of the flexible plate is in the range 60 to 750 GPa-um.

The device of any prior device claim, wherein the layer of uniform thickness sample is uniform over a lateral area that is at least 1 mm².

The device of any prior device claim, wherein the layer of uniform thickness sample is uniform over a lateral area that is at least 3 mm².

The device of any prior device claim, wherein the layer of uniform thickness sample is uniform over a lateral area that is at least 5 mm².

The device of any prior device claim, wherein the layer of uniform thickness sample is uniform over a lateral area that is at least 10 mm².

The device of any prior device claim, wherein the layer of uniform thickness sample is uniform over a lateral area that is at least 20 mm².

The device of any prior device claim, wherein the layer of uniform thickness sample is uniform over a lateral area that is in a range of 20 mm² to 100 mm².

The device of any prior device claim, wherein the layer of uniform thickness sample has a thickness uniformity of up to +/−5% or better.

The device of any prior device claim, wherein the layer of uniform thickness sample has a thickness uniformity of up to +/−10% or better.

The device of any prior device claim, wherein the layer of uniform thickness sample has a thickness uniformity of up to +/−20% or better.

The device of any prior device claim, wherein the layer of uniform thickness sample has a thickness uniformity of up to +/−30% or better.

The present invention finds use in a variety of different applications in various fields, where determination of the presence or absence, and/or quantification of one or more analytes in a sample are desired. For example, the present inventions finds use in the detection of atoms, molecules, proteins, peptides, nucleic acids, synthetic compounds, inorganic compounds, organic compounds, bacteria, virus, cells, tissues, nanoparticles, and the like. The sample can be a sample in various fields, that include, but not limited to, human, veterinary, agriculture, foods, environments, health, wellness, beauty, and others.

RELATED DOCUMENTS

The present invention includes a variety of embodiments, which can be combined in multiple ways as long as the various components do not contradict one another. The embodiments should be regarded as a single invention file: each filing has other filing as the references and is also referenced in its entirety and for all purpose, rather than as a discrete independent. These embodiments include not only the disclosures in the current file, but also the documents that are herein referenced, incorporated, or to which priority is claimed.

(1) Definitions The terms used in describing the devices, systems, and methods herein disclosed are defined in the current application, or in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

The terms "CROF Card (or card)", "COF Card", "QMAX-Card", "Q-Card", "CROF device", "COF device", "QMAX-device", "CROF plates", "COF plates", and "QMAX-plates" are interchangeable, except that in some embodiments, the COF card does not comprise spacers; and the terms refer to a device that comprises a first plate and a second plate that are movable relative to each other into different configurations (including an open configuration and a closed configuration), and that comprises spacers (except some embodiments of the COF card) that regulate the spacing between the plates. The term "X-plate" refers to one of the two plates in a CROF card, wherein the spacers are fixed to this plate. More descriptions of the COF Card, CROF Card, and X-plate are given in the provisional application Ser. Nos. 62/456,065, filed on Feb. 7, 2017, which is incorporated herein in its entirety for all purposes.

(2) Q-Card, Spacer and Uniform Sample thickness

The devices, systems, and methods herein disclosed can include or use Q-cards, spacers, and uniform sample thickness embodiments for sample detection, analysis, and quantification. In some embodiments, the Q-card comprises spacers, which help to render at least part of the sample into a layer of high uniformity. The structure, material, function, variation and dimension of the spacers, as well as the uniformity of the spacers and the sample layer, are herein disclosed, or listed, described, and summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

(3) Hinges, Opening Notches, Recessed Edge and Sliders

The devices, systems, and methods herein disclosed can include or use Q-cards for sample detection, analysis, and quantification. In some embodiments, the Q-card comprises hinges, notches, recesses, and sliders, which help to facilitate the manipulation of the Q card and the measurement of the samples. The structure, material, function, variation and dimension of the hinges, notches, recesses, and sliders are herein disclosed, or listed, described, and summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and US Provisional Application No. 62/456,504, which was filed on Feb. 8, 2017, all of which applications are incorporated herein in their entireties for all purposes.

(4) Q-Card, Sliders, and Smartphone Detection System

The devices, systems, and methods herein disclosed can include or use Q-cards for sample detection, analysis, and quantification. In some embodiments, the Q-cards are used together with sliders that allow the card to be read by a smartphone detection system. The structure, material, function, variation, dimension and connection of the Q-card, the sliders, and the smartphone detection system are herein disclosed, or listed, described, and summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

(5) Detection Methods

The devices, systems, and methods herein disclosed can include or be used in various types of detection methods. The detection methods are herein disclosed, or listed, described, and summarized in PCT Application (designating U.S.) Nos. PCT/US2016/045437 and PCT/US0216/051775, which were respectively filed on Aug. 10, 2016 and Sep. 14, 2016, US Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

(6) Labels

The devices, systems, and methods herein disclosed can employ various types of labels that are used for analytes detection. The labels are herein disclosed, or listed, described, and summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

(7) Analytes

The devices, systems, and methods herein disclosed can be applied to manipulation and detection of various types of analytes (including biomarkers). The analytes and are herein disclosed, or listed, described, and summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

(8) Applications (Field and Samples)

The devices, systems, and methods herein disclosed can be used for various applications (fields and samples). The applications are herein disclosed, or listed, described, and summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

(9) Cloud

The devices, systems, and methods herein disclosed can employ cloud technology for data transfer, storage, and/or analysis. The related cloud technologies are herein disclosed, or listed, described, and summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

Additional Notes

Further examples of inventive subject matter according to the present disclosure are described in the following enumerated paragraphs.

It must be noted that as used herein and in the appended claims, the singular forms "a", "an", and "the" include plural referents unless the context clearly dictates otherwise, e.g., when the word "single" is used. For example, reference to "an analyte" includes a single analyte and multiple analytes, reference to "a capture agent" includes a single capture agent and multiple capture agents, reference to "a detection agent" includes a single detection agent and multiple detection agents, and reference to "an agent" includes a single agent and multiple agents.

As used herein, the terms "adapted" and "configured" mean that the element, component, or other subject matter is designed and/or intended to perform a given function. Thus, the use of the terms "adapted" and "configured" should not be construed to mean that a given element, component, or other subject matter is simply "capable of" performing a given function. Similarly, subject matter that is recited as being configured to perform a particular function may additionally or alternatively be described as being operative to perform that function.

As used herein, the phrase, "for example," the phrase, "as an example," and/or simply the terms "example" and "exemplary" when used with reference to one or more components, features, details, structures, embodiments, and/or methods according to the present disclosure, are intended to convey that the described component, feature, detail, structure, embodiment, and/or method is an illustrative, non-exclusive example of components, features, details, structures, embodiments, and/or methods according to the present disclosure. Thus, the described component, feature, detail, structure, embodiment, and/or method is not intended to be limiting, required, or exclusive/exhaustive; and other components, features, details, structures, embodiments, and/or methods, including structurally and/or functionally similar and/or equivalent components, features, details, structures, embodiments, and/or methods, are also within the scope of the present disclosure.

As used herein, the phrases "at least one of" and "one or more of," in reference to a list of more than one entity, means any one or more of the entity in the list of entity, and is not limited to at least one of each and every entity specifically listed within the list of entity. For example, "at least one of A and B" (or, equivalently, "at least one of A or B," or, equivalently, "at least one of A and/or B") may refer to A alone, B alone, or the combination of A and B.

As used herein, the term "and/or" placed between a first entity and a second entity means one of (1) the first entity, (2) the second entity, and (3) the first entity and the second entity. Multiple entity listed with "and/or" should be construed in the same manner, i.e., "one or more" of the entity so conjoined. Other entity may optionally be present other than the entity specifically identified by the "and/or" clause, whether related or unrelated to those entities specifically identified.

Where numerical ranges are mentioned herein, the invention includes embodiments in which the endpoints are included, embodiments in which both endpoints are excluded, and embodiments in which one endpoint is included and the other is excluded. It should be assumed that both endpoints are included unless indicated otherwise. Furthermore, unless otherwise indicated or otherwise evident from the context and understanding of one of ordinary skill in the art.

In the event that any patents, patent applications, or other references are incorporated by reference herein and (1) define a term in a manner that is inconsistent with and/or (2) are otherwise inconsistent with, either the non-incorporated portion of the present disclosure or any of the other incorporated references, the non-incorporated portion of the present disclosure shall control, and the term or incorporated disclosure therein shall only control with respect to the reference in which the term is defined and/or the incorporated disclosure was present originally.

Additional Notes

Further examples of inventive subject matter according to the present disclosure are described in the following enumerated paragraphs.

It must be noted that as used herein and in the appended claims, the singular forms "a", "an", and "the" include plural referents unless the context clearly dictates otherwise, e.g., when the word "single" is used. For example, reference to "an analyte" includes a single analyte and multiple analytes, reference to "a capture agent" includes a single capture agent and multiple capture agents, reference to "a detection agent" includes a single detection agent and multiple detection agents, and reference to "an agent" includes a single agent and multiple agents.

As used herein, the terms "adapted" and "configured" mean that the element, component, or other subject matter is designed and/or intended to perform a given function. Thus, the use of the terms "adapted" and "configured" should not be construed to mean that a given element, component, or other subject matter is simply "capable of" performing a given function. Similarly, subject matter that is recited as being configured to perform a particular function may additionally or alternatively be described as being operative to perform that function.

As used herein, the phrase, "for example," the phrase, "as an example," and/or simply the terms "example" and "exemplary" when used with reference to one or more components, features, details, structures, embodiments, and/or methods according to the present disclosure, are intended to convey that the described component, feature, detail, structure, embodiment, and/or method is an illustrative, non-exclusive example of components, features, details, structures, embodiments, and/or methods according to the present disclosure. Thus, the described component, feature, detail, structure, embodiment, and/or method is not intended to be limiting, required, or exclusive/exhaustive; and other components, features, details, structures, embodiments, and/or methods, including structurally and/or functionally similar and/or equivalent components, features, details, structures, embodiments, and/or methods, are also within the scope of the present disclosure.

As used herein, the phrases "at least one of" and "one or more of," in reference to a list of more than one entity, means any one or more of the entity in the list of entity, and is not limited to at least one of each and every entity specifically listed within the list of entity. For example, "at least one of A and B" (or, equivalently, "at least one of A or B," or, equivalently, "at least one of A and/or B") may refer to A alone, B alone, or the combination of A and B.

As used herein, the term "and/or" placed between a first entity and a second entity means one of (1) the first entity, (2) the second entity, and (3) the first entity and the second entity. Multiple entity listed with "and/or" should be construed in the same manner, i.e., "one or more" of the entity so conjoined. Other entity may optionally be present other than the entity specifically identified by the "and/or" clause, whether related or unrelated to those entities specifically identified.

Where numerical ranges are mentioned herein, the invention includes embodiments in which the endpoints are included, embodiments in which both endpoints are excluded, and embodiments in which one endpoint is included and the other is excluded. It should be assumed that both endpoints are included unless indicated otherwise. Furthermore, unless otherwise indicated or otherwise evident from the context and understanding of one of ordinary skill in the art.

In the event that any patents, patent applications, or other references are incorporated by reference herein and (1) define a term in a manner that is inconsistent with and/or (2) are otherwise inconsistent with, either the non-incorporated portion of the present disclosure or any of the other incorporated references, the non-incorporated portion of the present disclosure shall control, and the term or incorporated disclosure therein shall only control with respect to the reference in which the term is defined and/or the incorporated disclosure was present originally.

The invention claimed is:

1. A device for changing temperature of a thin fluidic sample, comprising:
   a first plate, a second plate, spacers, and a clamp, wherein:
   (i) the first plate and the second plate are movable relative to each other into different configurations, including an open configuration and a closed configuration;
   (ii) each of the plates comprises, on its respective inner surface, a sample contact area for contacting a fluidic sample;
   (iii) one or both of the plates comprise the spacers on the inner surface thereof; and
   (iv) the spacers have a predetermined substantially uniform height that is equal to or less than 200 microns, wherein at least one of the spacers is inside the sample contact area
      wherein in an open configuration, the two plates are partially or completely separated apart, the spacing between the plates is not regulated by the spacers;
      wherein in a closed configuration, the two plates are operable to compress at least a part of the sample into a layer of substantially uniform thickness that is substantially stagnant relative to the plates, wherein the thickness of the layer is confined by the sample contact areas of the two plates and is regulated by the plates and the spacers;

wherein the inner surface of the first plate faces the inner surface of the second plate in the closed configuration;

wherein the clamp compresses the first plate and the second plate to fix the two plates together in the closed configuration, wherein the pressure of the clamp applied on the plates is 0.01 kg/cm² or higher;

wherein at least one of the first and second plates comprise a radiation absorbing layer that is configured to absorb electromagnetic wave from a radiation source and convert a substantial portion of the electromagnetic wave into heat and have an average ascending temperature ramp rate of at least 10° C./s; and wherein the radiation absorbing layer comprises a disk-coupled dots-on-pillar antenna (D2PA) array.

2. A device for changing temperature of a thin layer of a fluidic sample, comprising:

a first plate, a second plate, and spacers, wherein:
(i) the first plate has a thickness of 100 um (micron) or less;
(ii) the first plate and the second plate are movable relative to each other into different configurations, including an open configuration and a closed configuration;
(iii) each of the plates comprises, on its respective inner surface, a sample contact area for contacting a fluidic sample;
(iv) one or both of the plates comprise the spacers that are fixed to the respective inner surface thereof;
(v) the spacers have a predetermined substantially uniform height that is equal to or less than 200 microns;
(vi) at least one of the spacers is inside the sample contact area;

wherein in an open configuration, the two plates are partially or completely separated apart, the spacing between the plates is not regulated by the spacers; and wherein in a closed configuration, which is configured after the sample is deposited in the open configuration, at least a part of the sample is compressed by the two plates into a layer of substantially uniform thickness and is substantially stagnant relative to the plates, wherein the thickness of the layer is confined by the sample contact areas of the two plates and is regulated by the plates and the spacers;

wherein at least one of the first and second plates comprise a radiation absorbing layer that is configured to absorb electromagnetic wave from a radiation source and convert a substantial portion of the electromagnetic wave into heat and have an average ascending temperature ramp rate of at least 10° C./s; and wherein the radiation absorbing layer comprises a disk-coupled dots-on-pillar antenna (D2PA) array.

3. A device for changing temperature of a thin layer of a fluidic sample, comprising:

a first plate, a second plate, and a clamp, wherein:
(i) the first plate and the second plate are movable relative to each other into different configurations, including an open configuration and a closed configuration;
(ii) each of the plates comprises, on its respective surface, a sample contact area for contacting a fluidic sample to be assayed; and
(iii) the clamp compresses the first plate and the second plate to fix the plates at the closed configuration, wherein the pressure of the clamp applied on the plates is 0.01 kg/cm² or higher, wherein at least one of the first and second plates comprise a radiation absorbing layer that that is configured to absorb electromagnetic wave from a radiation source and convert a substantial portion of the electromagnetic wave into heat and have an average ascending temperature ramp rate of at least 10° C./s;

wherein the radiation absorbing layer comprises a disk-coupled dots-on-pillar antenna (D2PA) array;

wherein in an open configuration, the two plates are partially or completely separated apart, the average spacing between the plates is 250 μm or larger; and wherein in a closed configuration, which is configured after the sample is deposited in the open configuration, at least a part of the sample is compressed by the two plates into a layer of substantially uniform thickness and is substantially stagnant relative to the plates, wherein the thickness of the layer is confined by the sample contact areas of the two plates and is 200 μm thick or less.

4. The device of claim 1, wherein the radiation absorbing layer is near the at least part of the sample, whereas the area of the at least part of the sample and the radiation absorbing layer are substantially larger than the layer.

5. The device of claim 4, wherein the area of the at least part of the sample and the radiation absorbing layer are substantially larger than the uniform thickness of the sample.

6. The device of claim 1, wherein one of the first and second plates has a thickness of 100 μm or less.

7. The device of claim 1, wherein the radiation absorbing layer is near the at least part, wherein one of the first and second plates of a thickness of 100 μm or less.

8. The device of claim 2, wherein the clamp compresses the first plate and the second plate together in the closed configuration, wherein the pressure of the clamp applied on the plates is 0.01 kg/cm² or higher.

9. The device of claim 2, wherein the clamp that compresses the first plate and the second plate together in the closed configuration, and wherein the pressure of the clamp applied on the plates is 0.01 kg/cm² or higher.

10. A system for changing temperature of a thin fluidic sample layer, comprising:
(i) the device of claim 1,
(ii) a radiation source, wherein the radiation source is configured to radiate electromagnetic waves that the radiation absorbing layer absorbs significantly; and
(iii) a controller that is configured to control the radiation source and change the temperature of the sample.

11. A method for changing temperature of a layer of a fluidic sample, comprising:
(i) providing the system of claim 10;
(ii) depositing the fluid sample on one or both of the plates of the device when the plates are in the open configuration;
(iii) after (ii), pressing the plates into the closed configuration wherein the plates compress at least a part of the sample into the layer of a substantially uniform thickness less than 200 μm; and (iv) changing and maintaining the temperature of the layer by changing the presence, intensity, wavelength, frequency, and/or angle of the electromagnetic waves from the radiation source.

12. The device of claim 1, wherein the clamp is configured to comprise a heat insulator layer to reduce the heat conduction between the clamp and the plates, and wherein the heat insulator layer comprises a material of a thermal conductivity of 2 W/m-K.

13. The device of claim 3, wherein the clamp is configured to comprise a heat insulator layer, and wherein the heat insulator layer comprises a material of a thermal conductivity of 2 W/m-K.

14. The device of claim 3, wherein, in the closed configuration of the plates, the clamp prevents or reduces at least a part of the sample flow from one location of the plates to the other location of the plates.

15. The device of claim 1, wherein one of the first and second plates is flexible, the spacers have an inter-space-distance, the fourth power of the inter-spacer-distance (ISD) divided by a thickness (h) and a Young's modulus (E) of the flexible plate (ISD$^4$/(hE)) is $5\times10^6$ µm$^3$/GPa or less, and the thickness of the flexible plate times the Young's modulus of the flexible plate is in the range 60 to 750 GPa-um.

16. The device of claim 1, wherein, in the closed configuration of the first and second plates, the clamp has a thermal conduction contact with only the peripheral surface area of the plates.

17. The device of claim 1, wherein, in the closed configuration of the first and second plates, the clamp has a thermal conduction contact with only a surface area of the plates, wherein the surface area is outside the portion of the sample that nucleic acids to be amplified.

18. The device of claim 1, wherein the clamp comprises a window that is transparent allowing light outside going to the plates or the light inside plates going out.

19. The device of claim 1, wherein the clamp comprises a window that is transparent allowing light outside going to the plates or the light inside plates going out, wherein the transparence is above 30%, 40%, 50%, 60%, 70%, 80%, 90%, 100%, or a range between any two of the values.

20. The device of claim 1, wherein the clamp applies a pressure to compress the first plates and the second plates, wherein the pressure is 0.01 kg/cm$^2$, 0.1 kg/cm$^2$, 0.5 kg/cm$^2$, 1 kg/cm$^2$, 2 kg/cm$^2$, 5 kg/cm$^2$, 10 kg/cm$^2$, 20 kg/cm$^2$, 30 kg/cm$^2$, 40 kg/cm$^2$, 50 kg/cm$^2$, 60 kg/cm$^2$, 100 kg/cm$^2$, 150 kg/cm$^2$, 200 kg/cm$^2$, 400 kg/cm$^2$, or a range between any two of the values.

21. The device of claim 1, wherein the clamp applies a pressure to compress the first plates and the second plates, wherein the pressure is from 0.1 kg/cm$^2$ to 20 kg/cm$^2$.

22. The device of claim 6, wherein the clamp applies a pressure to compress the first and the second plates, wherein the pressure is from 0.1 kg/cm$^2$ to 20 kg/cm$^2$.

23. The device of claim 1, wherein the clamp applies a pressure to compress the first plates and the second plates, wherein the pressure is from 0.5 kg/cm$^2$ to 40 kg/cm$^2$.

24. The device of claim 2, wherein the clamp that compresses the first plate and the second plate together in the closed configuration, and the device further comprises a sealing material between at least part of the first plate and the second plate, and wherein the pressure of the clamp applied on the plates is 0.01 kg/cm$^2$ or higher.

25. The method of claim 11, wherein the changing temperature of the sample is a thermal cycling that changes the temperature up and down in cyclic fashion.

26. The method of claim 11, wherein the changing temperature of the sample is a thermal cycling, wherein the thermal cycling is for amplification of nucleic acid using polymerase chain action (PCR).

27. The method of claim 11, wherein the changing of the temperature of the sample is for isothermal amplification of nucleic acid.

28. The device of claim 4, wherein the radiation absorbing layer comprises a disk-coupled dots-on-pillar antenna (D2PA) array, silicon sandwich, graphene, superlattice or other plasmonic materials, or a combination thereof.

29. The device of claim 4, wherein the radiation absorbing layer comprises carbon or black nanostructures or a combination thereof.

30. The device of claim 4, wherein the radiation absorbing layer is configured to absorb radiation energy.

31. The device of claim 4, wherein the radiation absorbing layer is configured to radiate energy in the form of heat after absorbing radiation energy.

32. The device of claim 4, wherein the radiation absorbing layer is positioned underneath the sample layer and in direct contact with the sample layer.

33. The device of claim 4, wherein the radiation absorbing layer is configured to absorb electromagnetic waves selected from the group consisting of radio waves, microwaves, infrared waves, visible light, ultraviolet waves, X-rays, gamma rays, and thermal radiation.

34. The device of claim 4, wherein at least one of the first and second plates does not block the radiation that the radiation absorbing layer absorbs.

35. The device of claim 1, wherein one or both of the first and second plates have low thermal conductivity.

36. The device of claim 1, wherein the uniform thickness of the sample layer is regulated by one or more spacers that are fixed to one or both of the plates.

37. The method of claim 11, wherein the sample is a pre-mixed polymerase chain reaction (PCR) medium.

38. The device of claim 1, wherein the device is configured to facilitate PCR assays for changing temperature of the sample according to a predetermined program.

39. The device of claim 1, wherein the device is configured to conduct diagnostic testing, health monitoring, environmental testing, and/or forensic testing.

40. The device of claim 1, wherein the device is configured to conduct DNA amplification, DNA quantification, selective DNA isolation, genetic analysis, tissue typing, oncogene identification, infectious disease testing, genetic fingerprinting, and/or paternity testing.

41. The device of claim 1, wherein the sample layer is laterally sealed to reduce sample evaporation.

42. The system of claim 10, further comprising a controller, which is configured to control the presence, intensity, wavelength, frequency, and/or angle of the electromagnetic waves.

43. The system of claim 10, further comprising a thermometer, which is configured to measure the temperature at or in proximity of the sample contact area and send a signal to the controller based on the measured temperature.

44. The system of claim 43, wherein the thermometer is selected from the group consisting of: fiber optical thermometer, infrared thermometer, liquid crystal thermometer, pyrometer, quartz thermometer, silicon bandgap temperature sensor, temperature strip, thermistor, and thermocouple.

45. The system of claim 42, wherein the controller is configured to control the present, intensity, wavelength, frequency, and/or angle of the electromagnetic waves from the radiation source.

46. The system of claim 10, wherein the removal of the electromagnetic waves results in an average descending temperature rate ramp of at least 5° C./s.

47. The system of claim 10, wherein the radiation source and the radiation absorbing layer are configured to create an average descending temperature rate ramp of at least 5° C./s.

48. The system of claim 10, wherein the radiation source and the radiation absorbing layer are configured to create an average ascending temperature rate ramp of at least 10° C./s to reach the initialization step, the denaturation step and/or the extension/elongation step during a PCR, and an average descending temperature rate ramp of at least 5° C./s to reach the annealing step and/or the final cooling step during a PCR.

49. The device of claim 37, wherein the PCR sample comprises: template DNA, primer DNA, cations, polymerase, and buffer.

50. The method of claim 11, wherein the step of pressing the plates into the closed configuration comprises pressing the plates with an imprecise pressing force.

51. The method of claim 11, wherein the step of pressing the plates into the closed configuration comprises pressing the plates directly with human hands.

52. The method of claim 11, wherein the substantially uniform thickness of the layer of the sample has a thickness variation of less than 10%.

53. The method of claim 11, wherein the changing temperature of the sample is a thermal cycling, wherein the thermal cycling is for amplification of nucleic acid using polymerase chain reaction (PCR), that is selected from a group of hot-start PCR, nested PCR, touchdown PCR, reverse transcription PCR, RACE PCR, and digital PCR.

54. The method of claim 11, wherein the changing of the temperature of the sample is for isothermal amplification of nucleic acid, that is selected from a group of loop-mediated isothermal amplification, strand displacement amplification, helicase-dependent amplification, nicking enzyme amplification, rolling circle amplification, and recombinase polymerase amplification.

55. The system of claim 10, further comprising reagents selected from the group consisting of DNA template, primers, DNA polymerase, deoxynucleoside triphosphates (dNTPs), bivalent cations, monovalent cation, and buffer solution.

56. The device of claim 1, wherein each spacer has a substantially flat top.

57. The device of claim 1, wherein one of the first and second plates is 50 μm or less.

58. The device of claim 2, wherein the radiation absorbing layer is near the at least part of the sample of uniform thickness, whereas the area of the at least part of the sample and the radiation absorbing layer are substantially larger than the uniform thickness.

59. The device of claim 58, wherein the area of the layer and the radiation absorbing layer are substantially larger than the uniform-thickness of the layer.

60. The device of claim 3, wherein the radiation absorbing layer is near the at least part of the sample, whereas the area of the at least part of the sample and the radiation absorbing layer are substantially larger than the thickness of the layer.

61. The device of claim 60, wherein the area of the at least part of the sample and the radiation absorbing layer are substantially larger than the thickness of the layer.

62. The device of claim 1, wherein one of the first and second plates has a thickness of 100 μm or less.

63. The method of claim 11, wherein the radiation absorbing layer is near the at least part of the sample.

64. The device of claim 3, wherein the device has one of the first and second plates of a thickness of 100 μm or less.

65. The device of claim 3, wherein the radiation absorbing layer is near the at least part, where one of the first and second plates has a thickness of 100 μm or less.

66. A system for changing temperature of a thin fluidic sample layer, comprising:
  (i) a device of claim 2,
  (ii) a radiation source, wherein the radiation source is configured to radiate electromagnetic waves that the radiation absorbing layer absorbs significantly; and
  (iii) a controller configured to control the radiation source and change the temperature of the sample.

67. A method for changing temperature of a thin fluidic sample layer, comprising:
  (i) providing a system of claim 66;
  (ii) depositing a fluid sample on one or both of the plates of the device;
  (iii) after (ii), pressing the plates into a closed configuration wherein the plates compress at least a part of the sample into a layer of a thickness less than 200 μm; and
  (iv) changing and maintaining the temperature of the sample layer by changing the presence, intensity, wavelength, frequency, and/or angle of the electromagnetic waves from the radiation source.

68. A system for changing temperature of a thin fluidic sample layer, comprising:
  (i) a device of claim 3,
  (ii) a radiation source, wherein the radiation source is configured to radiate electromagnetic waves that the radiation absorbing layer absorbs significantly; and
  (iii) a controller configured to control the radiation source and change the temperature of the sample.

69. A method for changing temperature of a thin fluidic sample layer, comprising:
  (i) providing a system of claim 68;
  (ii) depositing a fluid sample on one or both of the plates of the device;
  (iii) after ii, pressing the plates into a closed configuration wherein the plates compress at least a part of the sample into a layer of a thickness less than 200 μm; and
  (iv) changing and maintaining the temperature of the sample layer by changing the presence, intensity, wavelength, frequency, and/or angle of the electromagnetic waves from the radiation source.

70. A system for changing temperature of a thin fluidic sample layer, comprising:
  (i) a device of claim 60,
  (ii) a radiation source, wherein the radiation source is configured to radiate electromagnetic waves that the radiation absorbing layer absorbs significantly; and
  (iii) a controller configured to control the radiation source and change the temperature of the sample.

71. A method for changing temperature of a thin fluidic sample layer, comprising:
  (i) providing a system of claim 70;
  (ii) depositing a fluid sample on one or both of the plates of the device;
  (iii) after ii, pressing the plates into a closed configuration wherein the plates compress at least a part of the sample into a layer of a thickness less than 200 μm; and
  (iv) changing and maintaining the temperature of the sample layer by changing the presence, intensity, wavelength, frequency, and/or angle of the electromagnetic waves from the radiation source.

72. The device of claim 3, wherein, in the closed configuration of the plates, the clamp prevents or reduces at least a part of the sample flow from one location of the plates to the other location of the plates.

73. The device of claim 3, wherein, in the closed configuration of the plates, the clamp is configured to have thermal conduction contact with a part of the surface of the plates.

74. The device of claim 3, wherein, in the closed configuration of the plates, the clamp has a thermal conduction contact with only the peripheral surface area of the plates.

75. The device of claim 3, wherein, in the closed configuration of the plates, the clamp has a thermal conduction contact with only a surface area of the plates, wherein the surface area is outside the portion of the sample that nucleic acids to be amplified.

76. The device of claim 3, wherein the clamp comprises a window that is transparent allowing light outside to go to the plates or the light inside plates going out.

77. The device of claim 3, wherein the clamp comprises a window that is transparent allowing light outside to go to the plates or the light inside plates going out, wherein the transparence is above 30%, 40%, 50%, 60%, 70%, 80%, 90%, 100%, or a range between any two of the values.

78. The device of claim 3, wherein the clamp is capable of a pressure to compress the first plates and the second plates, wherein the pressure is 0.01 kg/cm$^2$, 0.1 kg/cm$^2$, 0.5 kg/cm$^2$, 1 kg/cm$^2$, 2 kg/cm$^2$, 5 kg/cm$^2$, 10 kg/cm$^2$, 20 kg/cm$^2$, 30 kg/cm$^2$, 40 kg/cm$^2$, 50 kg/cm$^2$, 60 kg/cm$^2$, 100 kg/cm$^2$, 150 kg/cm$^2$, 200 kg/cm$^2$, 400 kg/cm$^2$, or a range between any two of the values.

79. The device of claim 3, wherein the clamp is capable of a pressure to compress the first plates and the second plates, wherein the pressure is from 0.1 kg/cm$^2$ to 20 kg/cm$^2$.

80. The device of claim 3, wherein the clamp is capable of a pressure to compress the first plates and the second plates, wherein the pressure is from 0.1 kg/cm$^2$ to 20 kg/cm$^2$.

81. The device of claim 3, wherein the clamp is capable of applying a pressure to compress the first plates and the second plates, wherein the pressure is from 0.5 kg/cm$^2$ to 40 kg/cm$^2$.

82. The device of claim 3, wherein one or both of the first and second plates have low thermal conductivity.

83. The device of claim 3, wherein the uniform thickness of the sample-layer is regulated by one or more spacers that are fixed to one or both of the first and second plates.

84. The device-method of claim 67, wherein the sample is a pre-mixed polymerase chain reaction (PCR) medium.

85. The device of claim 3, wherein the device is configured to facilitate PCR assays for changing temperature of the sample according to a predetermined program.

86. The device of claim 3, wherein the device is configured to conduct diagnostic testing, health monitoring, environmental testing, and/or forensic testing.

87. The device of claim 3, wherein the device is configured to conduct DNA amplification, DNA quantification, selective DNA isolation, genetic analysis, tissue typing, oncogene identification, infectious disease testing, genetic fingerprinting, and/or paternity testing.

88. The device of claim 3, wherein the sample layer is laterally sealed to reduce sample evaporation.

89. The device of claim 3, wherein the spacer has a substantially flat top.

90. The device of claim 1, wherein the spacers are periodically arranged.

* * * * *